US006492165B1

(12) United States Patent
Callahan et al.

(10) Patent No.: US 6,492,165 B1

(45) Date of Patent: Dec. 10, 2002

(54) RETROVIRUS ISOLATED FROM HUMANS

(75) Inventors: Margaret E. Callahan, Decatur, GA (US); Thomas M. Folks, Snellville, GA (US); Paul Sandstrom, Kanata (CA); Shambavi Subbarao, Doraville, GA (US); Jennifer Brown, Sacramento, CA (US); Walid Heneine, Atlanta, GA (US); William M. Switzer, Stone Mountain, GA (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 09/692,652

(22) Filed: Oct. 19, 2000

Related U.S. Application Data

(63) Continuation-in-part of application No. 09/367,213, filed as application No. PCT/US98/02598 on Feb. 12, 1998, which is a continuation-in-part of application No. 08/798,071, filed on Feb. 12, 1997, now Pat. No. 5,882,192.

(51) Int. Cl.$^7$ .......................... C12N 15/00; C12N 5/06

(52) U.S. Cl. .................................. 435/320.1; 435/339

(58) Field of Search .............................. 435/339, 320.1

(56) References Cited

U.S. PATENT DOCUMENTS

| | | | |
|---|---|---|---|
| 5,108,920 A | 4/1992 | Ng et al. | 435/239 |
| 5,459,056 A | 10/1995 | Powell et al. | 435/240.2 |
| 5,597,896 A | 1/1997 | Montagnier et al. | 530/388.35 |
| 5,646,032 A | 7/1997 | Meulen et al. | 435/325 |
| 5,882,912 A | 3/1999 | Sandstrom et al. | 435/235.1 |

FOREIGN PATENT DOCUMENTS

| | | |
|---|---|---|
| DE | 43 18387 A1 | 8/1994 |
| WO | WO 98/35024 | 8/1998 |
| WO | WO 00/77177 | 12/2000 |

OTHER PUBLICATIONS

Anonymous Survey for Simian Immunodeficiency Virus (SIV) Seropositivity in SIV—Laboratory Researchers—United States, 1992. *MMWR Morb. Mort. Wkly Rep.* 41(43):814–815 (Oct. 30, 1992).

Chapman et al. Xenotransplantation and xenogeneic infections. *N. Engl. J. Med.* 333:1498–1501 (Nov. 30, 1995).

DHHS Docket No. 96M–0311. Draft Public Health Service (PHS) Guideline on Infectious Disease Issues in Xenotransplantation. *Federal Register* 61(185):49919–49932 (Sep. 23, 1996).

EMBL Database; EMVRL: AF049085; Accession No. AF049085 (Aug. 3, 1998).

EMBL Database; EMVRL; AF049084; Accession No. AF049084 (Aug. 3, 1998).

(List continued on next page.)

*Primary Examiner*—Hankyel T. Park

(74) *Attorney, Agent, or Firm*—Needle & Rosenberg, P.C.

(57) ABSTRACT

The present invention comprises spumavirus isolated from humans. More specifically, the spumavirus of the present invention was isolated from humans who had exposure to nonhuman primates. Importantly, the spumavirus of the present invention or antibodies to the spumavirus can be used to detect the presence of spumavirus or antibodies in body fluids, for pathogenicity studies of related viruses, and as a vector for gene therapies. The spumavirus of the invention can also be used for treatment of conditions in humans due to the presence of rapidly dividing cells and for recombinant live virus vaccination.

10 Claims, 5 Drawing Sheets

OTHER PUBLICATIONS

Heneine et al. Absence of evidence for human spumaretrovirus sequences in patients with Graves' disease [letter]. *J. Acq. Immune Defic. Synd. & Human Retrov.* 9(1):99–101 (1995).

Heneine et al. Identification of a human population infected with simian foamy viruses. *Nat. Med.* 4(4):403–407 (Apr. 1998).

Heneine et al. Lack of evidence for infection with known human and animal retroviruses in patients with chronic fatigue syndrome. *Clin. Infec. Dis.* 18(Suppl. 1):S121–125 (1994).

Neumann–Haefelin et al. Nonhuman Primate Spumavirus Infections Among Persons with Occupational Exposure—United States, 1996. *MMWR Morb. Mort. Wkly Rep.* 46(6):129–131 (Feb. 14, 1997).

Neumann–Haefelin et al. Foamy viruses. *Intervirology* 35:196–207 (1993).

Perspectives in Disease Prevention and Health Promotion Guidelines to Prevent Simian Immunodeficiency Virus Infection in Laboratory Workers and Animal Handlers. *MMWR Morb. Mort. Wkly Rep.* 37(45):693–694and 699–704 (Nov. 18, 1988).

Schweizer et al. Phylogenetic Analysis of Primate Foamy Viruses by Comparison of *pol* Sequences. *Virology* 207:577–582 (1995).

Schweizer et al. Absence of foamy virus DNA in Graves' disease. *AIDS Res. & Human Retrov.* 10(5):601–605 (1994).

Simonsen et al. Absence of evidence for infection with the human spuma retrovirus in an outbreak of meniere–like vertiginous illness in Wyoming, USA [letter]. *Acta Otolaryngol* (*Stockh*) 114:223–224 (1994).

Khabbaz et al. Simian immunodeficiency virus needlestick accident in a laboratory worker. *Lancet* 340:271–273 (1992).

Khabbaz et al. Brief report: Infection of a laboratory worker with simian immunodeficiency virus. *N. Eng. J. Med.* 330:172–177 (1994).

"Reactivity of primate sera to foamy virus Gag and Bet proteins", Hahn et al., *Journal of General Virology*, (1994), 75, 2635–2644.

"Phylogenetic Analysis of Primate Foamy Viruses by Comparison of *pol* Sequences", Schweizer and Neumann–Haefelin, *Virology* 207, 577–582, (1995).

"Genomic Organization and Expression of Simian Foamy Virus Type 3 (SFV–3)", Renne et al., *Virology* 186, 597–608, (1992).

"Transduction of Hematopoietic Cells by Foamy Virus Vectors", Hirata et al., *Blood*, vol. 88, No. 9, (Nov. 1), 1996, pp. 3654–3661.

"Foamy Virus Vectors", Russell and Miller, *Journal of Virology*, vol. 70, No. 1, Jan. 1996, pp. 217–222.

"Detection of Reverse Transcriptase By A Highly Sensitive Assay In Sera From Persons Infected With Human Immunodeficiency Virus Type 1", Walid Heneine, et al., *The Journal of Infectious Diseases*, May 1995, pp. 1210–1216.

"Spumaviruses", Philip C. Loh, *The Retroviridae*, vol. 2, 1993, pp. 361–397.

"Cell tropism of the simian foamy virus type 1 (SFV–1)", Ayalew Mergia et al., *Journal of Medical Primatology*, Jul. 21, 1995, pp. 2–7.

"Isolation of Novel Human Endogenous Retrovirus–Like Elements with Foamy Virus–Related *pol* Sequence", Agnes Cordonnier et al., *Journal of Virology*, vol. 69, No. 9, Sep. 1995, pp. 5890–5897.

"Identification and Characterization of the Bel 3 Protein of Human Foamy Virus", Jakob Weissenberger and Rolf M. Flugel, *Aids Research and Human Retroviruses*, vol. 10, No. 5, 1994.

"Human Foamy Virus Polypeptides: Identification of *env* and *bel* Gene Products", Marie–Louise Giron et al., *Journal of Virology*, vol. 67, No. 6, Jun. 1993, pp. 3596–3600.

"Isolation, Cloning, and Sequencing of Simian Foamy Viruses from Chimpanzees (SFVcpz); High Homology to Human Foamy Virus (HFV)", Ottmar Herchenroder et al., *Virology* 201, 1994, pp. 187–199.

"Isolation of a New Foamy Retrovirus from Orangutans", Myra O. McClure et al., *Journal of Virology*, vol. 68, No. 11, Nov. 1994, pp. 7124–7130.

"Specific enzme–linked immunosorbent assey for the detection of antibodies to the human spumavirus", Christoph Mahnke et al., *Journal of Virological Methods*, 29, 1990, pp. 13–22.

"The Foamy Viruses," John J. Hooks et al., *Bacteriological Reviews*, Sep. 1975, vol. 39, No. 3, pp. 169–185.

"Simian Foamy Virus Isolated from an Accidentally Infected Human Individual", Matthias Schweizer et al., *Journal of Virology*, Jun. 1997, vol. 71, No. 6, pp. 4821–4824.

"No Evidence of Antibody to Human Foamy Virus in Widespread Human Populations", Munaf Ali et al., *Aids Research and Human Retroviruses*, vol. 12, No. 15, 1996, pp. 1473–1483.

"Markers of Foamy Virus Infections in Monkeys, Apes, and Accidentally Infected Humans: Appropriate Testing Fails to Confirm Suspected Foamy Virus Prevalence in Humans", Matthias Schweizer et al., *Aids Research and Human Retroviruses*, vol. 11, No. 1, 1995, pp. 161–170.

"Persistent Zoonotic Infection of a Human with Simian Foamy Virus in the Absence of an Intact *orf–2* Accessory Gene", Margaret E. Callahan et al., *Journal of Virology*, Nov. 1999, vol. 73, No. 11, pp. 9619–9624.

SIMIAN FOAMY VIRUS PERCENT NUCLEOTIDE IDENTITY

| | Case1 | Case2 | Case3 | SFV 3 AGM | SFV BAB | SFV MAC | HFV | SFV CPZ | SFV PYG | SFV8 SPM |
|---|---|---|---|---|---|---|---|---|---|---|
| Case1 | - | 82.6 | 82.1 | 87.5 | 82.4 | 77.4 | 68.7 | 66.6 | 67.2 | 66.4 |
| Case2 | - | - | 95.5 | 81.7 | 92.7 | 76.2 | 68.3 | 66.4 | 68.9 | 62.3 |
| Case3 | - | - | - | 82.1 | 93.9 | 76.9 | 67.5 | 66.5 | 69.3 | 62.3 |

FIG. 5

RETROVIRUS ISOLATED FROM HUMANS

CROSS REFERENCE TO RELATED APPLICATIONS

This application is a continuation-in-part of U.S. patent application Ser. No. 09/367,213, filed on Dec. 8, 1999 (national phase application of PCT application Ser. No. PCT/US98/02598, filed Feb. 12, 1998) which is a continuation-in-part of U.S. patent application Ser. No. 08/798,071, filed Feb. 12, 1997, now U.S. Pat. No. 5,882, 192.

This invention was made by the Centers for Disease Control and Prevention, an agency of the United States Government.

TECHNICAL FIELD

The present invention relates to a novel retrovirus, a spumavirus, that has been isolated from humans. More particularly, the novel spumavirus may be used as a vector for gene therapy. The novel spumavirus may also be used as a recombinant live virus vaccine.

BACKGROUND OF THE INVENTION

Spumavirus, also known as foamy virus for the characteristics of vacuolization the virus induces in cell culture, belongs to a distinct group of retroviruses. The simian foamy viruses (SFVs) include isolates from Old World and New World monkeys and are classified into 10 different serotypes based on serological cross-reactivities. Virus appears to persist in the host for a long period of time in a latent form and can exist in the presence of neutralizing antibody.

Currently the most studied retrovirus, Human Immunodeficiency Virus, is believed to be derived from nonhuman primate transmission into humans at some past time. Concerns about the risk of transmission of retroviruses from non-human primates to humans working in research laboratories were heightened in the early 1990's when two persons developed antibodies to SIV (Simian Immunodeficiency Virus) following work-related exposures, one of whom had clear evidence of persistent viral infection. (See CDC. Anonymous survey for simian immunodeficiency virus (SIV) seropositivity in SIV laboratory researchers—United States, 1992. MMWR Morb Mort Wkly Rep 1992; 41: 814–5; Khabbaz R. F., et al. Brief report: infection of a laboratory worker with simian immunodeficiency virus. New Eng J Med. 1994; 330: 172–7; Khabbaz R F, et al. Simian immunodeficiency virus needlestick accident in a laboratory worker. Lancet 1992; 340: 271–3; and CDC. Guideline to prevent simian immunodeficiency virus infection in laboratory workers and animal handlers. MMWR 1988; 37:693–704.) In addition to SIV, nonhuman primate species used in biomedical research are commonly infected with SFV (simian foamy virus), STLV (simian t-cell lymphotrophic virus), and/or type D retroviruses. All of these retroviruses cause lifelong infections in nonhuman primates, and some are known to be transmissible through sexual contact, blood, or breast feeding. Natural SFV infections in non-human primates have not been definitively associated with disease. In non-human primates, infection with the other retroviruses may result in a clinical spectrum ranging from asymptomatic infection to life threatening immunodeficiency syndromes or lymphoproliferative disorders. The transmission routes of SFVs among non-human primates remain undefined, but the prevalence of seroreactivity is high among captive adult non-human primates.

Studies of the prevalence of spumavirus infection of humans are limited and the findings are not definitive.

Though there is some evidence of human infection with SFV (antibodies and positive PCR results), such occurrence has been reported in only two persons, both of whom had occupational risks for infection. Associated disease was not reported in either. (See Schweizer M., et al. Absence of foamy virus DNA in Graves' disease. AIDS Res & Human Retrov 1994; 10: 601–5; Neumann-Haefelin D, et al., Foamy viruses. Intervirology 1993; 35: 196–207; and Schweizer M, et al., Markers of foamy virus infections in monkeys, apes, and accidentally infected humans: appropriate testing fails to confirm suspected foamy virus prevalence in humans. AIDS Res & Human Retrov 1995; 11: 161–70.) There have been no published reports that virus was ever isolated from these infected individuals.

Other inconclusive evidence was seen in early studies which described a relatively high rate of seroreactivity to antibodies to spumaviruses among human populations not known to be exposed to non-human primates. In some instances seroreactivity was suggestively linked to human disease, including disorders of the central nervous system, thyroid disease, and Chronic Fatigue Syndrome. In most instances these studies lacked definitive evidence of human infection and were not subsequently confirmed. (See Heneine W, et al., Absence of evidence for human spumaretrovirus sequences in patients with Graves' disease [letter]. J Acq Immune Defic Synd & Human Retrov. 1995; 9: 99–101; Simonsen L, et al.,. Absence of evidence for infection with the human spumaretrovirus in an outbreak of Meniere-like vertiginous illness in Wyoming, USA [letter]. Acta Oto-Laryngologica 1994; 114: 223–4; and Heneine W., et al., Lack of evidence for infection with known human and animal retroviruses in patients with chronic fatigue syndrome. Clin Infect Dis 1994; 18: S121–5).

To the knowledge of the inventors, there has not been a documented, definitive isolation of a spumavirus, such as the one of the present invention, from humans. Previous reports of human spumavirus isolates are now widely regarded as laboratory contaminants.

Recent publications indicate that earlier serological tests showing human spumavirus antibodies in the human population were incorrect. Immunological investigation of a previously reported human spumavirus revealed that it shared common antigens in complement fixation, immunofluorescence and neutralization assays with the chimpanzee foamy virus, SFV-6. Furthermore, failure to detect serological evidence of HFV infection in people from a wide geographical area suggested that this virus isolate was a variant of SFV-6, particularly since sera from chimpanzees naturally infected with SFV-6 neutralized both viruses. In a survey for prevalence of human foamy virus in more than 5000 human sera, collected from geographically diverse populations, none of the serum samples were confirmed as positive. Taken together with sequence analysis endorsing the phylogenetic closeness of the purported human spumavirus to SFV-6/7, these data strongly suggest that human foamy virus is not naturally found in the human population. (See Ali, M. et al., "No Evidence of Antibody to Human Foamy Virus in Widespread Human Populations," AIDS Research and Human Retroviruses, Vol. 12, No. 15, 1996.)

Recent concern that xenotransplantation, the use of living tissues from nonhuman species in humans for medical purposes, may introduce new infections into the human community has increased the importance of defining the ability of simian retroviruses to infect and/or cause disease in humans (See Chapman L E, et al. Xenotransplantation and xenogeneic infections. New Engl J Med 1995; 333: 1498–1501; DHHS. Docket No. 96M-0311. Draft Public Health Service (PHS) Guideline on Infectious Disease Issues in Xenotransplantation. Federal Register Vol.61, No. 185. Sep. 23, 1996.). The primary animal species considered as donors for xenografts are baboons and pigs. Thus, what is needed are compositions and methods for detecting viruses that may be transmitted from the nonhuman organ donors to the recipient human. Additionally, information regarding these transmissible agents may provide valuable information about the organ donors' cellular receptors that may be important for transplantation success.

Gene therapies have long looked for a good vector that can transport the foreign gene of choice into human cells. The lack of any known disease associated with the virus of the present invention makes the present invention an ideal candidate for gene therapy regimens. Thus, compositions and methods for gene therapy are needed that use a vector capable of carrying a significant amount of foreign DNA that will enter the host organism and not cause disease.

Compositions and methods for vaccination using recombinant live retroviruses are also needed. A live virus, that causes no illness in humans, and that has genes of antigens of choice incorporated into its genome, would provide for an excellent vaccination tool. The retrovirus would reproduce in the human host and expose the immune system to antigens so that an immune response can be initiated.

Targeted attack on reproducing cells is a goal of cancer treatment. What is needed is are compositions and methods for cancer treatment that are specific for dividing cells that do not cause systemic damage to the cancer patient. A virus that could infect and kill dividing cells, without killing other cells of the host would provide a solution for cancer treatment.

SUMMARY OF THE INVENTION

The present invention is directed to compositions and methods comprising a novel spumavirus or foamy virus, known as SVFHu-1. The present invention comprises a spumavirus isolate of human origin that has been definitively isolated from a human with no disease. The novel spumavirus of the present invention has been maintained through tissue culture cells where it causes the characteristic vacuolation of the cells that is known for foamy viruses.

The novel spumavirus of the present invention has utility as a reagent for the immunological screening of the human population for the prevalence of such viruses in the population. The novel spumavirus of the present invention can also serve as a vector in gene therapy because the virus appears to cause no disease in humans and is not transmitted to other humans. Additionally, the novel spumavirus of the present invention can be used as a reagent in pathogenicity studies of these and related viruses. Moreover, the sequences of the novel spumavirus of the present invention can be used as probes to detect virus in biological samples. Vectors include, but are not limited to, procaryotic, eucaryotic and viral vectors. The foamy virus of the present invention can also be used as a live recombinant virus vaccine. Additionally, the spumavirus of the present invention can be used as a replicating viral system to kill live dividing cells, either in vitro or in vivo.

The spumaviruses or foamy viruses are by far the least well characterized of the retroviruses. They have been isolated as agents that cause vacuolation ("foaming") of cells in culture from a number of mammalian species, including monkeys, cattle, cats, and reportedly in humans. Persistent infection with these viruses is not associated with any known disease.

Recent studies using improved diagnostic assays have shown no evidence of foamy virus infection of humans in studies of large populations (approximately 8,000 persons). Given these results, the identification of seroreactivity in three persons occupationally exposed to non-human primates is notable. The PCR identification of viral genome sequences in biologic specimens from all three, and isolation of the virus from one, confirm virus infection in these workers.

The present invention includes the isolation and characterization of a spumavirus, SVFHu-1, that was shown to have been transmitted from non-human primates to humans at some point in the past. The spumavirus of the present invention does not appear to be readily transmitted from human to human. The spumavirus of the present invention can be used in constructing protocols for diagnosing spumavirus infections and may be used as a vector in gene therapy procedures.

The present invention also includes methods and compositions for detecting spumavirus in biological fluids. The methods and compositions, including kits, can be in any configuration well known to those of ordinary skill in the art. The present invention also includes antibodies specific for the spumavirus and antibodies that inhibit the binding of antibodies specific for the spumavirus. These antibodies can be polyclonal antibodies or monoclonal antibodies, which also includes fragments of any type of antibody. The antibodies specific for the spumavirus can be used in diagnostic kits to detect the presence and quantity of spumavirus in biological fluids or in organs from nonhuman primates for xenotransplantation. Antibodies specific for spumavirus may also be administered to a human or animal to passively immunize the human or animal against spumavirus, thereby reducing infection after accidental exposure to nonhuman primate bodily fluids.

The present invention also includes compositions and methods, including kits, for detecting the presence and quantity of antibodies that bind spumavirus in body fluids. The methods, including kits, can be in any configuration well known to those of ordinary skill in the art. Such kits for detection of spumavirus itself or detection of antibodies to the spumavirus can be used to monitor the blood supply for the presence of spumavirus in the blood supply.

The present invention also includes methods and compositions comprising recombinant live virus vaccines. The virus of the present invention has areas of its genome that make it ideal for the insertion of exogenous genes. The genes can code for any protein for which vaccination or gene therapy is desired. Because SFVHu-1 replicates at a higher level than other known foamy viruses, it is capable of providing a high level of antigen to the host carrying the virus. After administration of SFVHu-1 to the host, the virus would infect the cells, replicate and provide protein antigens to the immune system of the host. A novel aspect of such recombinant live viruses is that SFVHu-1 does not cause disease in the host organism. Additionally, there is no transmission from one host organism to other non-infected host organisms, even by close contact with exchange of bodily fluids. The recombinant live virus vaccines of the present invention are a safe way to provide antigen in a most optimum method to the immune system.

The present invention further includes methods and compositions for the use of replicating viral system to kill live dividing cells in a host or in vitro. In in vitro uses, SFVHu-1 can be used to detect and kill rapidly dividing cells. Foamy viruses, including SFVHu-1, can infect a wide variety of species of cells and can be used in many in vitro cell systems. For example, if the assay of the in vitro cell system required the identification of quiescent cells, application of SFVHu-1 to the tissue culture system would result in the selection of the rapidly dividing cells by SFVHu-1. The tissue culture cells would be infected, but because SFVHu-1 has a productive infection and cytopathic effects only in dividing cells, the dividing cells are killed by such dividing cells would be infected by SFVHu-1 and killed by such infection. The remaining non-dividing cells of the culture would remain alive.

In a host, the ability of SFVHu-1 to infect dividing cells provides an excellent treatment for conditions due to the presence of rapidly dividing cells. For example, a person with disease due to rapidly dividing cells, such as cancer or any known angiogenic condition, could be infected with SFVHu-1. Such virus may or may not carry other, exogenous genes for other effects in the host. Because SFVHu-1 does not cause disease in the host and there is no transmission of the virus to contacts with the host, only the person with the disease from rapidly dividing cells will be treated. In addition, only the rapidly dividing cells of that host person will be infected by SFVHu-1, and the rest of the body will remain uninfected. The virus will infect the rapidly dividing cells and kill them. For example, a person with a fast growing tumor would be infected with SFVHu-1 and the cells of the tumor would be destroyed by the virus. The SFVHu-1 can be recombinantly modified to be selective for cellular receptors on the tumor to make the virus even more specifically targeted to just those cells.

Such treatment with SFVHu-1 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels.

Accordingly, it is an object of the present invention to provide a composition comprising a novel spumavirus.

It is another object of the present invention to provide a method of detecting a spumavirus.

It is yet another object of the present invention to provide methods and compositions for detecting the presence and amount of spumavirus in a body fluid or organ.

A further object of the present invention is to provide compositions and methods for treating genetic and physiologic disorders using gene therapy techniques comprising the novel spumavirus of the present invention as a vector for nucleic acid sequences and antisense sequences.

Another object of the present invention is to provide compositions and methods useful for manipulating the expression of genes.

Yet another object of the invention is to provide vaccines.

Yet another object of the present invention is to provide compositions and methods for treating viral infections in humans or animals.

Another object of the present invention is to provide compositions and methods that are effective in treating genetic diseases.

Yet another object of the present invention is to provide a method of treating microbial infections in humans or animals.

It is another object of the present invention to provide for treatments of conditions that are caused in part by rapidly dividing cellular growth.

Another object of the present invention is to provide live recombinant virus vaccines.

An object of the present invention is to provide diagnostic tools such as antibodies or antigens for the monitoring of the blood supply or organ and tissue donation for the presence of spumavirus.

These and other features and advantages of the present invention will become apparent after a review of the following detailed description of the disclosed embodiments and the appended claims.

BRIEF DESCRIPTION OF THE DRAWINGS

FIG. 5 is a comparison of the nucleotide homology of the sequenced portion of the present invention and other retroviruses.

DETAILED DESCRIPTION OF THE INVENTION

Figure 1:
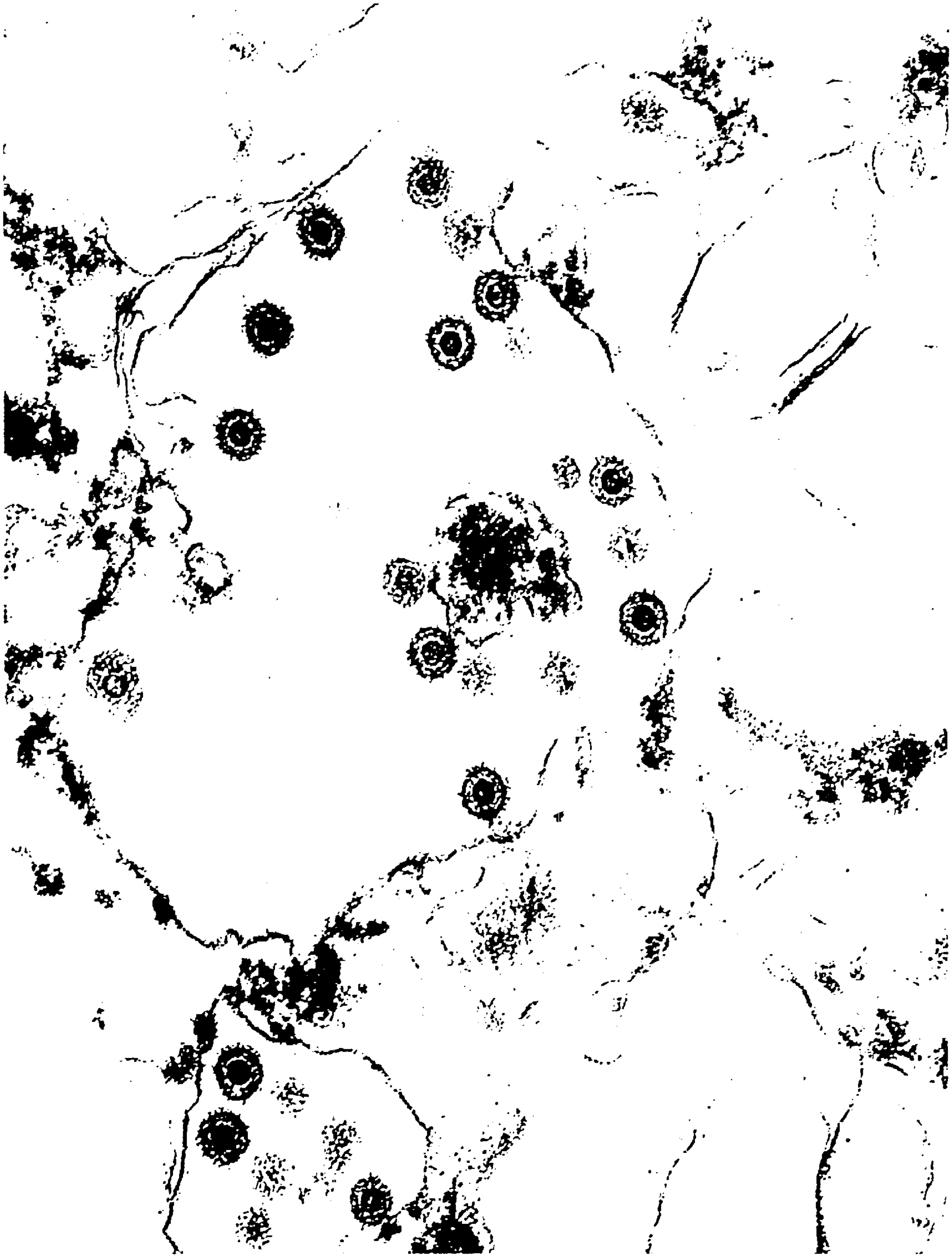
FIG. 1 shows a transmission electron microscope photomicrograph of viral particles in Cf2Th canine thymocytes.

In response to the identification of simian immunodeficiency virus infection in an occupationally exposed workers, Centers for Disease Control and National Institutes for Health collaborated in an anonymous serosurvey of persons with similar work exposures. Simian immunodeficiency virus seroreactivity was present in 3/427 (0.64%) stored serum samples from these anonymous workers (See CDC. Anonymous survey for simian immunodeficiency virus (SIV) seropositivity in SIV laboratory researchers—United States, 1992. MMWR *Morb Mort Wkly Rep* 1992; 41: 814–5; Khabbaz RF, et al.,. Brief report: infection of a laboratory worker with simian immunodeficiency virus. *New Eng J Med*. 1994; 330: 172–7). Consequently, a voluntary testing and counseling program was developed that allowed linkage between specific exposures or health outcomes and serostatus of persons occupationally exposed to simian immunodeficiency virus. The workers enrolled in this voluntary linked prospective simian immunodeficiency virus surveillance are also at occupational risk for exposure to other retroviruses common in nonhuman primates (nonhuman primates).

Therefore, in 1995, the linked surveillance was expanded to include voluntary testing and counseling for exposure to simian spumaviruses (more commonly called simian foamy viruses, or SFV), simian T-lymphotropic viruses (STLV), and simian type D retroviruses. 1,823 samples from 13 institutions in the United States had been tested for simian immunodeficiency virus; samples from 231 of the participating volunteer workers were also tested for other retroviruses from non-human primates. Three of these 231 workers (1.3%) were determined to be infected with a SFV-like virus by serology and PCR.

An immunofluorescent assay that was developed using cells infected with SFV serotype 3 identified antibodies to a SFV-like virus in recently collected serum specimens from all three workers. The 3 specimens were also western blot positive, showing reactivity to both p70 and p74 gag precursor bands of SFV-3 antigen. Repeat testing of additional sera obtained from these 3 workers at later time points are also positive in both assays. (These workers or cases are herein identified individually as Case A, Case B, and Case C.)

Additional blood samples from these three cases were tested for SFV proviral DNA sequences using polymerase chain reaction (PCR) assays employing primer sets from two regions of the polymerase gene that are conserved among known primate foamy viruses. All three cases were PCR positive in both regions. The PCR products from one region were sequenced. The sequences from each case were distinct from each other but all showed greater than 80% homology to known non-human primate foamy virus sequences. The partial sequences, produced with DNA polymerase PCR primer, of the viral sequence of the present invention is shown below. Seq. ID 1 is a viral DNA sequence isolated from infected Cf2Th cells and Seq. ID 2 is a viral DNA sequence isolated from PBLs from Case A. There is 99.76% homology between the two sequences. The corresponding RNA sequences and resulting proteins can be deduced from these sequences.

Seq. ID 1

TTACTACAAGGACAATATCCAAAAG-
GTTTTCCAAAACAATATCAAT ATGA
ACTTAATGAAGGACAAGTTATAG-
TAACTCGTCCTAATGGACAAAG AATTA
TTCCTCCAAAATCAGACAGGCCTCAAAT-
TATTTTGCAAGCACATAA TATT
GCACATACAGGAAGAGATTCAAC-
CTTTCTTAAGGTCTCTTCCAAG TATTG
GTGGCCAAATCTTAGAAAGGATGTGGT-
TAAAGTTATCAGACAATG TAAGC
AATGTCTGGTCACAAATGCAGCTACCT-
TAGCTGCGCCTCCAATAC TGAGG
CCTGAAAGACCTGTAAAGC-
CTTTTGATAAATTTTTTGTTGACTATA TTGG
CCCTTTACCCCCTTCTAATGGGTACTTA-
CATGTCCTTGTAGTAGTC GATG
GTATGACTGGATTTGTATGGTTA

Seq.ID 2

TTACTACAAGGACAATATCCAAAAG-
GTTTTCCAAAACAATATCAAT ATGA
ACTTAATGAAGGACAAGTTATAG-
TAACTCGTCCTAATGGACAAAG AATTA
TTCCTCCAAAATCAGACAGGCCT-
CAAATTTTGCAAGCACATAA TATT
GCACATACAGGAAGAGATTCAAC-
CTTTCTTAAGGTCTCTTCCAAG TATTG
GTGGCCAAATCTTAGAAAGGATGTGGT-
TAAAGTFATCAGACAATG TAAGC
AATGTCTGGTCACAAATGCAGCTACCT-
TAGCTGCGCCTCCAATAC TGAGG**
CCTGAAAGACCTGTAAAGC-
CTTTTGATAAATTTTTTGTTGACTATA TTGG
CCCTTTACCCCCTTCTAATAGGTACTTA-
CATGTCCTTGTAGTAGTC GATG
GTATGACTGGATTTGTATGGTTA

The relationship between each of the isolates and other known spumaviruses is shown in FIG. 5 which is a phylogenetic tree showing the percent homology of the nucleotide sequences ot these viruses and in FIG. 6.

The 5' end of the LTR of SFVHu-1, of 1567 nucleotide bases, has also been sequenced, and is shown as Seq. ID 3.

```
 1 TTCCCAATAAACATCATCCT GGGTGGACTA GACATCTTAC
TAAATTCAAG

51ATATCTAGATTCTCCACTCCTGCTGATGTCCAGAAAATTG
TGGATGAGCT

101TCTCCCTAGAGGAGCAAGCATTGTAATGCCTGATGGAACAAA
GTATCCAA

151GTACCAGAAAAGTGCACTTAGTCAATGAAGGAACCCTTGTAG
AATACCAA

201
GCCAAATGTAAGGAGATAGAGGAAAAGTACGGAGGATGCTTTTC
TACAGA

251
TAGTGATGAT GACAGTGATG ATTACTCTGA GGATACTCCA
GAAACTGAAA

301
CCACTGATGT GGAATAGAGT ACAGTGTTAA GGATTCACAT
AATCTGCCTA

351
GCAACTGCTT ATGCTTAAGA ATGAATCAGT ATATTGTTTA
GGAATAAGTT

401
ATAGTTTATA AGAAGTTAAT CCTTAGGGAG TATTTGGTGG
AAATGACTGA

451
GTGACATGAA GTTTATTCAC CATACTCTCA ATAGGAGCCA
CTAGTTGAGC

501
CTGTGCGTTC AAATCCATGC TCAGCTTAAG TGACTCCCTT
TTAGTTTCAC

551
TTFAAGTTAA GTTAGGAATA AGTTCCATAT AATCCTAAGG
GAGTATGTGG

601
ACCTTCTTGT TAGGAAATAG TFTAAGATAG TCCACAGCTC
CCTTCTTTTT

651
GAGTTCTAGT CTTTGTTAAG TFTGTTGGCT CATACAGATA
AAGTGCTCAT

701
TAAACAGGAA ACCGCAACCG GGTAAAGGTT AGCACAGTAA
ATTAAGCTAG

751
CAGTTACTCA AGAGCCCGGT AAGCATTCAA GTAGTTCGAA
TCCCTTTAAT

801
GCTGACGGAT TGCTCTTTAG TGAGGTGATG TAATCTGTTT
TTGCAATCTG

851
AAATGTGTGT TTGCACAGGA AGTTGTACAA GAAAGGGAAT
GGCTAAACTT

901
GTTACAGTTC GAACAAACAT TTAGCAATTT CCTTTGCTTT
TGGAGTTCGA
```

-continued

951
GCCTTGTACT TATACTTTGA GCATATGTAT TGTAACACCT
AAGTATGGAA

1001
AAATCTCCAA GTATGAGTCA CGAGATGCTT GGCTCACTGC
GTTGGACGAC

1051
TGGAAAGAAG CTTCAACAGT CGGGACAGCA TCTCGAAGAA
GGCCTCCGGA

1101
ATGAAAGAGT GAAAAATGAA GTCTCCTCAT TCAGAGAGCC
TTCTFTTAGA

1151
ATTTCAGGCA GAATAGAGTT TCCAATAGAA TAAAGITITG
TATTAGCAGA

1201
TAGATAGGAT ATATAATCTC TGCTTTAGAT TGTACGGGAG
CTCACCACTA

1251
CTCGCTGCGT CGAGAGTGTT CGAGTCTCTC CAGGCTTGGT
AAGATATAAA

1301
CTTTGGTATT CTCTGTATTC TTATGATCCA ATATTACTCT
GCTTATAGAT

1351
TGTAATGGGC AATGGCAATG CTTTATCAAT GAATGATTTT
ATGGTGAATT

1401
AAGTTCATAT ATGTTTTAAG AAGTTTAACA ATAAACCGAC
TTAATTCGAG

1451
AACCAGATTF ATTAGTATTG TCTCTTTCTA TACTTFAAGT
AAAGTGAAAG

1501
GAGTTGTATA TTAGCCTTGC TTATAAGAGC CATCTAGTGG
TATAAGTGTG

1551 TACTACACTT ATCTAAA

A 3'internal region of SFVHu-1 has also been sequenced. This sequence includes ORF1(Open Reading Frame) and ORF-2, which are overlapping genes, and includes 3' sequence from env and bel genes. This sequence is identified as Seq. ID. 4 and contains 2406 nucleotides. This sequence is analogous to SFV-3 bases 8953 to 11,356.

Seq.ID.4
1
AAGGGGATGT TGAGCAATCC AACATGTGCA TACCCACTFG
AATCATCITA

51
AAACCATGTF ACTAATGAGG AAGATFGACT GGACTFTFAT
TAAGAGTGAT

101
TGGATFAAAG AACAACTTCA GAAAACTGAA GATGAAATGA
AGATFATFAG

151
AAGAACAGCT AAAAGTTFAG TATATFATGT GACTCAAACA
TCATCTTCCA

201
CTACAGCAAC ATCATGGGAA ATFGGAATFT ATTATGAAAT
AACTATACCA

-continued

251
AAACATATTF ATFTGAATAA TFGGCAAGTF GTTAACATAG
GTCATCTGAT

301
TGAGTCAGCT GGTCATFTGA CCTTAATAAG GGTTAAACAT
CCTTATGAAG

351
ACTTTAATAA AGAATGCACA TATGAACAAT ATTTACATCT
TGAAGACTGC

401
ATATCTCAGG ATFATGTGAT TFGTGACACG GTACAAATAT
TGTCACCATG

451
TGGAAACTCA ACAGTAACCA GTGACTGCCC TGTCACTGCT
GAAAAGGTAA

501
AGGAACCATA TATFCAAGTG TCAGCTFTAA AAAATGGAAG
CTATTFGGTt

551
CTAACCAGTA GAACAGATFG CTCAATACCA GCATATGTFC
CCAGCATTGT

601
AACTGTGAAC GAAACAGTFA AGTGJTITGG GGTFGAGTTF
CATAAACCAC

651
TATACTCAGA AAGTAAAGTC AGCTTTGAAC CACAAGTTCC
ACATCTGAAA

701
CTACGCTTGC CACATCTGGT TGGGATTATT GCAAGTCTTC
AAAATTTGGA

751
AATTGAAGTA ACNAGCACCC AAGAGAGTAT ANAAGATCAG
ATTGAAAGAG

801
TTCAATCACA GCTTCTTCGG CTGGACATTC ACGAGGGAGA
CTTTCCTGCT

851
TGGATTCAAC AACTTGCTTC TGCAACCAAG GACGTCTGGC
CTGCAGCTGC

901
TAAAGCTCTT GAAGGCATAG GTAACTTTTT ATCTAATACT
GCCCAGGGAA

951
TATTTGGAAC TGCTGTAAGT ATTCTATCCT ATGCCAAGCC
TATTCTTATA

1001
GGAATAGGTG TTATACTTTT GATTGCATTC TTGTTTAAGA
TTGTATCATG

1051
GCTTCCTGGG AAGAAGAAAA AGAACTAGGA CATCTGCATC
TTCCAGAAGA

1101
CGATCCTCTG CCCAATTTAG ATGTGCTCCT GGGTCTTGAT
CATATGGAAT

1151
CCAATGAAGG ACCTGATCAA AATCCAGGAG CTGAAAAGAT
CTACATTCAA

1201
CTCCAAGCAG TCCCAGGGGA AGCCTCAGAG AAAACITACA
AATTTGGATA

-continued

1251
TGAAGACAAA GAGGCACAAA ATCCTGACTT AAAAATGAGA
AATTGGGTTC

1301
CTAACCCCGA CAAAATGAGT AAGTGGGCCT GTGCAAGGCT
TATTCTTTGT

1351
GGACTTTATA ATGCAAAAAA GGCTGGAGAA CTCTTGGCTA
TGGACTATAA

1401
TGTTCAATGG GAACAATCAA AAGAAGACCC AGGATACTTT
GAAGTGGAAT

1451
ATCACTGTAA AATGTGCATG ACTGTTATTC ATGAACCTAT
GCCTATCCAA

1501
TATGATGAAA AAACTGGATT ATGGCTAAAA ATGGGTCCCC
TTAGGGGAGA

1551
TATAGGATCT GTAGTACATA CTTGTAGAAG GCATTACATG
AGATGTTTGT

1601
CTGCCCTTCC TAGCAATGGA GAACCTCTCA AACCTAGAGT
CCGGGCTAAT

1651
CCTGTCCGAA GATATCGAGA GAAGCAAGAG TTCGTTGCGA
CTAGGCCTAA

1701
ACGCTCCAGA TGGGGTGTGG CCCCTAGCGC AGACTCCCAT
ACTTCCAGTG

1751
GTGACGCCAT GGCCCTTATG CCAGGACCAT GCGGCCCCTT
CGGTATGGAC

1801
ACTCCTGGTT GCTTACTGGA AGGGATACAA GGATCAGGGC
CTGGAACCTC

1851
CGAAATGGCT GTGGCAATGT CAGGAGGACC TTTCTGGGAA
GAAGTGTACC

1901
GGGACTCAAT TCCTGGTGCC CCCACTGGGT CTAGTGAAAA
TTAGGCTTTA

1951
TCAAAATCTA ACTGTTGTAA ATGTTTGTGG ATCTGTTGAC
CCATGGGAAA

2001
ATGAGAATCC CACTAGAGGT CGCAGAGGGC CTATGCATAG
ATATGATTGT

2051
AGAATTGCTT GTGATCCAAG CTATTGCTTT AAGGCTATFT
GGGAAGGAAA

2101
CTTTTGGGAC AAAAAAAAAA GGATCAGGCA TGCTGGCTAG
TTCATCTGAA

2151
AGAAGGACAT AAATTTGGTG CAGATGAGTT ATCTTCTGGG
GATCTTAAAA

2201
TATTAGCAGA ATCTAGACCT TATCCATATG GATCTATTGG
TCATTGTGCT

-continued

2251
ATGCTTCAAT ATGCAGTACA AGTTAAAATG AGAGTTGATA
GAGCTCCTTT

2301
GACCTCAAAG GTGAGAGCTA TTAAAGCTTT GCACTATCAT
CGCTGGAATA

2351
TTTGTCAGCT GGAAAATCCT GGCATAGGAG AAGGATTCAG
TCCCTCTGGT

2401 AATACACA

The entire sequence of SFVHu-1 has been sequenced. The entire sequence is Seq. ID 5.

1
TGTGGCTGAC AGCTACTAAA ATGATTGGCA CCCAGGAATC
AGACTATTGG

51
CATGAGTACA AAAGATGGGG ATATTTCCCT TTGATTCCAA
ATAAACATCA

101
TCCTGGGTGG ACTAGACATC TTACTAAATT CAAGATATCT
AGATTCTCCA

151
CTCCTGCTGA TGTCCAGAAA ATTGTGGATG AGCTTCTCCC
TAGAGGAGCA

201
AGCATTGTAA TGCCAGATGG AACAAAGTAT CCAAGTACCA
GAAAAGTGCA

251
CTTAGTCAAT GAAGGAACCC TTGTAGAATA CCAAGCCAAA
TGTAAGGAGA

301
TAGAGGAAAA GTACGGAGGA TGCTTTTCTA CAGATAGTGA
TGATGACAGT

351
GATGATTACT CTGAGGATAC TCCAGAAACT GAAACCACTG
ATGTGGAATA

401
GAGTACAGTG TTAAGGATTT ACATAATCTG CCTAGCAACT
GCTTATGCTT

451
AAGAATGAAT CAGTATATTG TTTAGGAATA AGCCTTAGTT
TATAAGTAGT

501
TAATCCTTAG GGAGTATTTG GTGGAAATGA CTGAGTGACA
TGAAGTTTAT

551
TCACCATACT CTCAATAGGA GCCACTAGTT GAGCCTGTGC
GTTCAAATCC

601
ATGCTCAGCT TAAGTGACTC CCTTTTAGTT TCACTTTAAG
TTAAGTTAGG

651
AATAAGTTCC ATATAATCCT AAGGGAGTAT GTGGACCTTC
TTGTTAGGAA

701
ATAGTTTAAG ATAGTCCACA GCTCCCTTCT TTTTGAGTTC
TAGTCTTTGT

-continued

751
TAAGTTTGTT GGCTCATACA GATAAAGTGC TCATTAAACA
GGAAACCGCA

801
ACCGGGTAAA GGTTAGCACA GTAAATTAAG CTAGCAGTTA
CTCAAGAGCC

851
CGGTAAGCAT TCAAGTAGTT CGAATCCCTT TAATGCTGAC
GGATTGCTCT

901
TTAGTGAGGT GATGTAATCT GTTTTTGCAA TCTGAAATGT
GTGTTTGCAC

951
AGGAAGTTGT ACAAGAAAGG GAATGGCTAA ACTTGTTACA
GTTCGAACAA

1001
ACATTTAGCA ATTTCCTTTG CTTTTGGAGT TCGAGCCTTG
TACTTATACT

1051
TTGAGCATAT GTATTGTAAC ACCTAAGTAT GGAAAAATCT
CCAAGTATGA

1101
GTCACGAGAT GCTTGGCTCA CTGCGTTGGA CGACTGGAAA
GAAGCTTCAA

1151
CAGTCGGGACAGCATCTCGA AGAAGGCCTC CGGAATGAAA
GAGTGAAAAA

1201
TGAAGTCTCC TCATTCAGAG AGCCTTCTTT TAGAATTTCA
GGCAGAATAG

1251
AGTTTCCAAT AGAATAAACT TTTGTATTAG CAGATAGATA
GGATATATAA

1301
TCTCTGCTTT AGATTGTACG GGAGCTCACC ACTACTCGCT
GCGTCGAGAG

1351
TGTTCGAGTC TCTCCAGGCT TGGTAAGATA TAAACTTTGG
TATTCTCTGT

1401
ATTCTTATGA TCCAATATTA CTCTGCTTAT AGATTGTAAT
GGGCAATGGC

1451
AATGCTTTAT CAATGAATGA TTTTATGGTG AATTAAGTTC
ATATATGTTT

1501
TAAGAAGTTT AACAATAAAC CGACTTAATT CGAGAACCAG
ATTTATTAGT

1551
ATTGTCTCTT TCTATACTTT AAGTAAAGTG AAAGGAGTTG
TATATTAGCC

1601
TTGCTTATAA GAGCCATCTA GTGGTATAAG TGTGTACTTA
CACTTATCTA

1651
AAGAGGTGGA ATTCTTTAAG GATAACCAAT ATACAAAATT
CCACGACAAT

1701
TGGCGCCCAA CGTGGGGCTC GAATATAAGT CGGGTTTTAT
TATAAAGACT

-continued

1751
TGTTTAAGTC TTAGAATTAT CCCTAGGGAC CTTCACGCAC
TGCGGAAGGT

1801
ATAAGTACTC AAAGATGGGT GATCATAATT TGAATGTTCA
AGAACTCTTG

1851
AACCTTTTTC AGAATCTAGG TATTTCCAGA CAACCAAATC
ATAGAGAAGT

1901
CRTAGGACTT CGTATGACAG GAGGCTGGTG GGGTCCAGGG
ACCCGCTATA

1951
ATCTAGTTTC AATCTTTTTA CAAGATGATT CTGGACAACC
TTTACAACAA

2001
CCCAGGTGGA GACCTGAAGG TAGACCAGTT AATCCTTTGG
TTCATAATAC

2051
TATAGAAGCC CCTTGGGGAG ACTTAAGGTT AGCTTTTGAA
GACTTGGATG

2101
TAGCAGAAGG TACTTTGAGG TTTGGTCCTT TAGCTAATGG
AAATTGGATT

2151
CCTGGAGATG AATACTCCAT GGAATTCCAG CCTCCACTAG
CACAAGAAAT

2201
AGCTCAATTA CAAAGAGACG AAATGGAAGA AATATTGGAT
ATAACAGGAC

2251
AAATATGTGC ACAAGTTATA GATTTAGTAG ATATGCAAGA
TGCTCAAATT

2301
AGAGGCCYTG AAAGACGTTT ACAAGATAGA CCAGGTTTAA
GGGATAACTT

2351
ACCAGTTGCT GGTATACAAG CACCACCATC TAGTCCAATT
GGGCAGCCTA

2401
TTGCATCATC TTCACTTCAA CCTGTTCCTG GATCCAGCCA
ATCCTCTGCT

2451
GATCTTGGTT GGGAATCAGG AGCGCCTGGG CAAATAGATC
CTAGATTGTC

2501
CAGGGTGGCC TATAACCCAT TTTTACCAGG ACCAAGTGAT
GGGTCTGGGG

2551
GATCAATCCC AGTCCAGCCT AGTGCTCCTC CAGCGGTTCT
TCCATCCTTA

2601
CCCTCACTTC CTGCACCTGT TGCTCAACCT GTTGTTCAGT
ATGTTGTTCC

2651
ACCTGCCCCT GCTCCACAAG CTATTCCAAT TCAACACATT
CGAGCAGTGA

2701
CAGGAAATAC ACCTACTAAT CCAAGAGATA TTCCTATGTG
GCTTGGAAGA

-continued

2751
CATTCAGCTG CTATAGAAGG AGTATTTCCT ATGACTACGC CTGATCTTCG

2801
CTGTCGAGTT GTTAATGCTC TTATAGGAGG AAGTCTTGGA CTTTCTTTGG

2851
AGCCTATACA TTGTGTAAAT TGGGCTGCTG TTGTAGCTGC TCTATATGTG

2901
AGAACACATG GATCATATCC CATACATGAA CTAGCTAATG TACTCCGAGC

2951
AGTTGTTAAT CAAGAGGGAG TAGCAACAGG TTTTCAACTT GGAATTATGC

3001
TGTCCAATCA AGATTTTAAT CTTGTTTGGG GAATTCTACG TCCCCTATTG

3051
CCTGGACAAG CTGTAGTCAC AGCTATGCAG CAAARACTTG ATCAAGAAGT

3101
CAGTGACGCT GCTAGGATTG CCTCCTTTAA TGGACATTTA AATGATATAT

3151
ATCAACTTCT AGGACTGAAT GCCCGAGGTC AAAGCATTAC TAGAACTCAG

3201
GGTAGTTCAA TCTCTGGAAC CTCTACTTCT ACAGGCAGAG GAAGGAGAGG

3251
ACAAAGAAAC CAGCAACAGT CTGGTCAACA GCAACAACAA CAGGCAAGAA

3301
GAAGTAATCA GGGAAACCAG AGACAGAGAA ATAATAATCA GAGACAATCC

3351
TCTGGTAATA ATCAGGGACA AGGAGGCCAA GGAGGATATA ATTTGAGACC

3401
CAGAACTTATCAGCCGCAGCGCTACGGAGG AGGACGTGGA AGAAGATGGA

3451
ACGATAATCA ACAACAGCAA CAAGCACAGC CAGGCAGATC AGCTGATCAA

3501
CCTCGTTCCC AGAGTCAGCA ACCACAAACA GAGGCTCGTG GCGATCAGTC

3551
ACGAACATCTGGTGCTGGGCGCGGACAACA AGGARGAGGG AACCAAAACC

3601
GAAATCAACG CCGGGCTGAT GCTAACAATA CTCGGAATGT GGATACTGTG

3651
ACAGTAACCA CAACTTCCTC CTCCACAACT GGTTCGGGTC AAAATGGATC

3701
CTCTACAGCT CCTCCAGCCC CTGGAAGCAG AAATCAAGGG GACTAAATTA

-continued

3751
AAGGCTCATT GGGACAGTGG AGCTACAGTA ACATGTGTTC CACAAGCCTT

3801
TCTAGAAGAT GAAGTACCAA TTAAAAATAT TTGGATCAAG ACAATTCATG

3851
GTGAAAAAGA ACAGCCTGTC TATTATTTAA CCTTTAAAAT MCAAGGAAGA

3901
AAAGTAGAAG CAGAAGTAAT CTCTTCCCCT TATGACTACA TATTAGTCAG

3951
TCCATCTGAC ATCCCCTGGC TAATGAAGAA ACCTCTCCAA TTGACAACTT

4001
TAGTTCCTCT TCAAGAATAC AAAGAAAGAC TTTTAAAGCA AACTATTTTA

4051
ACTGAAAAAT ATAAAGATAG ATTACAATCT TTATTTTTGA AATATGATGC

4101
ATTATGGCAA CATTGGGAAA ATCAAGTGGG CCATAGGCGT ATTAAGCCTC

4151
ATCATATAGC AACTGGTACA GTTAACCCTA GACCACAAAA GCAATATCCA

4201
ATTAATCCAA AAGCAAAGCC AAGTATACAA GTTGTAATTA ATGATTTATT

4251
AAAACAAGGT GTGCTAATAC AGCAAAATAG TGTGATGAAT ACTCCTGTAT

4301
ATCCTGTACC AAAACCAGAT GGAAAATGGA GAATGGTTTT AGATTATAGA

4351
GAAGTCAATA AGACCATCCC TTTAATTGCA GCTCAAAATC AACATTCTGC

4401
AGGGATTCTA TCATCCATAT TTAGAGGCAA ATATAAAACC ACTTTAGATT

4451
TATCTAATGG TTTTTGGGCT CATTCTATTA CACCAGAATC TTATTGGTTA

4501
ACTGCTTTTA CTTGGCTTGG ACAACAATAT TGTTGGACAA GATTACCTCA

4551
AGGATTTCTC AATAGTCCTG CTTTATTTAC AGCAGATGTT GTTGATTTAT

4601
TAAAAGAAGT ACCAAATGTA CAAGTTTATG TGGATGATAT TTATATTAGT

4651
CATGATGACC CTGAAGAACA TTTGGACCAA CTTGAGAAAG TGTTTTCGCT

4701
ATTGCTCAAA TGCGGTTATG GGGTTTCTCT TAAAAAATCT GAAATTGCTC

-continued

4751
AACATGAAGT TGAATTCCTT GGGTTTAATA TTACAAAAGA
AGGTCGAGGC

4801
CTAACAGAAA CTTTTAAACA AAAACTCTTA AATATAACTC
CACCAAAAGA

4851
TCTGAAACAG TTACAAAGTA TTTTAGGCCT TCTAAATTTT
GCAAGGAACT

4901
TTGTTCCTAA TTTTTCTGAA TTAGTTAAAC CCTTATATAA
TATCATTGCT

4951
AATGCCAATG AGAAATATAT TACATGGACT TCTGACAATA
GTCAACAGCT

5001
ACAATATATA ATTTCATTAT TAAATTCTGC AGAAAACTTA
GAAGAAAGAA

5051
ATCCAGAAGT CAGATTAATA ATGAAAGTAA ATACCTCTCC
TTCAGCAGGA

5101
TATATACGGT TTTATAATGA ATTTGCTAAA AGACCTATTA
TGTACTTGAA

5151
TTATGTTTAT ACTAAGGCAG AAGTTAAGTT CACTAACACT
GAAAAATTGC

5201
TAACTACTAT ACATAAAGGG TTAATTAGAG CCTTAGATCT
TGCCATGGGA

5251
CAAGAAATCT TAGTATATAG TCCTATCGTA TCCATGACCA
AAATTCAAAA

5301
AACACCATTA CCAGAAAGAA AAGCTCTACC AATTAGATGG
ATAACCTGGA

5351
TGTCTTATTT AGAAGATCCC AGAATACAAT TTCATTATGA
TAAGACATTA

5401
CCCGAGCTAC AACAGGTTCC TACTGTCACT GATGATGTTA
TAGCTAAGAC

5451
TAAACATCCT AGTGAATTTA ATATGGTCTT CTACACTGAT
GGTTCTGCAA

5501
TCAGACATCC AAATGTTAAT AAGTCACATA GTGCTGGAAT
GGGTATTGCT

5551
CAAGTACAGT TTAAACCTGA GTTTACAGTT GTTAATACTT
GGTCTATTCC

5601
TCTTGGAGAT CATACGGCAC AACTTGCCGA AGTTGCAGCT
GTAGAATTTG

5651
CATGTAAAAA GGCCCTCAAA ATAGATGGAC CTGTTTTAAT
AGTAACTGAT

5701
AGTTTCTATG TTGCTGAGAG TGCTAATAAG GAATACCYT
ATTGGCAATC

-continued

5751
AAATGGGTTC TTTAATAACA AAAAGAAACC CCTTAAACAT
GTCTCCAAGT

5801
GGAAGTCAAT TGCAGAATGT GTACAATTAA AGCCTGACAT
TACTATTATT

5851
CATGAAAAAG GTCACCAGCC TACTGCTTCA ACATTTCATA
CAGAAGGTAA

5901
TAATTTAGCT GATAAGCTTG CCACCCAAGG AAGTTATGTG
GTAAATACAA

5951
ATACCACTCC AAGCCTGGAT GCAGAGTTGG ATCAATTACT
ACAAGGACAA

6001
TATCCAAAAG GTTTTCCAAA ACAATATCAA TATGAACTTA
ATGAAGGACA

6051
AGTTATAGTA ACTCGTCCTA ATGGACAAAG AATTATTCCT
CCAAAATCAG

6101
ACAGGCCTCA AATTATTTTG CAAGCACATA ATATTGCACA
TACAGGAAGA

6151
GATTCAACCT TTCTTAAGGT CTCTTCCAAG TATTGGTGGC
CAAATCTTAG

6201
AAAGGATGTG GTTAAAGTTA TCAGACAATG TAAGCAATGT
CTGGTCACAA

6251
ATGCAGCTAC CTTAGCTGCG CCTCCAATAC TGAGGCCTGA
AAGACCTGTA

6301
AAGCCTTTTG ATAAATTTTT TGTTGACTAT ATTGGCCCTT
TACCCCCTTC

6351
TAATRGGTAC TTACATGTCC TTGTAGTAGT CGATGGTATG
ACTGGATTTG

6401
TATGGTTATA CCCCACTAAG GCTCCTTCAA CTGGCGCAAC
TGTTAAAGCT

6451
CTCAATATGC TCACTAGTAT TGCAGTTCCA AAGGTGATAC
ACTCTGATCA

6501
GGGTACAGCA TTCACCTCTG CAACTTTTGC TGATTGGGCA
AAAGACAAAG

6551
GTATACATTT GGAATTCAGT ACTCCTTACC ATCCCCAAAG
TAGTGGCAAG

6601
GTGGAAAGGA AAAATAGTGA TATAAAACGA CTTTTAACTA
AACTGCTTGG

6651
TGGGAGACCT GCTAAGTGGN ATGACCTTCT TTCAGTTGTT
CAATTGGCAT

6701
TAAATAATTC ATATAGGCCT CTTTCTTCTA AATATACTCC
TCATCAACTT

-continued

6751
TTGTTTGGTA TAGATTCAAA TACACCATTT GCAAACTCTG ATACACTTGA

6801
TTTATCAAGA GAAGAAGAAC TCTCTCTTTT ACAGGAAATC AGAACTTCTC

6851
TTTGCCATCC ATCCTCCCCT CCTGCCTCCG TTCGTGTCTG GTCTCCTTCT

6901
GTTGGCCAAT TGGTCCAGGA GAGGGTAGCC AGGCCTGCAT CTTTAAGACC

6951
TCGGTGGCAT AAACCTACTC CTGTTCTGGA AGTCATTAAT CCACGAACTG

7001
TTGTCATTTT GGACCATCTT GGCAACAGGA GAACTGTAAG TGTGGATAAT

7051
TTAAAATTAA CARCTTATCA GAAGGATGGC ACCTCCAATG AATCTGCAGC

7101
AATGGCTATT GTGGAAAAAG ATGAATGAAG CACATTCAGC GTTAGAGAAT

7151
ATTTCAACCC TTACTGAAGA ACAGAAGCAA CAAGTGATTA TTGAGATTCA

7201
ACAAGAAGAA GTAATACCTA CTAGGATGGA CAGAGTAAAG TATCTAGCAT

7251
ATGCATGTTG TGCTACCAGT ACACGTGTCA TGTGTTGGTT ATTTTTGATT

7301
TGTGTGTTGC TAATTATTGT ATTTGTATCT TGTTTTGTCA CTGTTGCTAG

7351
GATTCAATGG AATAAGGATA TTACTGTGTT TGGACCAGTC ATTGATTGGA

7401
ATGTTACCCA TCAAGCAACA TATCAACAGC TTAGAGCTTC CAGAATAGCT

7451
AGATCTTTAA GGGTAGAACA TCCTCATATA TCATATATAT CAATAAATAT

7501
GTCTAGTATA CCACAAGGTG TTATATATAC ACCTCACCCT GAACCTATAA

7551
TCCTCAAGGA GAGGGTTTTA GGGATTTCTC AGGTGTTAAT GATAAATTCT

7601
GAAAATATAG CTAATGTGGC CAATTTGTCT CAAGACACAA AAGTATTGTT

7651
GACTGATATG ATAAATGAGG AATTACAAGA TTTGTCAAAC CAAATGATTG

7701
ACTTCGAATT ACCTCTAGGA GATCCTAGAG ACCAAAATCA ATATGTACAT

-continued

7751
CATAAGTGTT ACCAGGAGTT TGCTCATTGT TATTTAGTCA AATATAAAAC

7801
ACNTAAAGAA TGGCCCTCTT CAGCTCTGAT TGCTGATCAG TGTCCCCTAC

7851
CAGGAGAACA TCCAACTGTA CAGTATTCAC ATCAAAATAT ATGGGACTAT

7901
TATGTTCCTT TTCAACAAAT ACGGCCAGAG AAATGGACTT CATCCTTAGT

7951
ATATGAAGAT GCTACAATAG GGAGCTTCTA TATACCAAAA AATATGAGAA

8001
ACAAGAATGT TACACATGTA ATATTTTGTT CAGATCAATT ATATGGAAAA

8051
TGGTATAATT TGATGAATAC TGTACAAGAA AATGAACAAA TTCAAGTCAT

8101
AAAATTAAAA AATATTACCA AATCGGGTAC CTCTCAAGTT AAGGATAGAG

8151
GACTTCCGTC CGCTTGGCAT AAGAATGGTA AAAGTACATA TTTTAGGCCT

8201
ATTAATACTT TGGATATTTG TAATAGACCT GAGTTAGTAT TATTACTCAA

8251
TAGTACTTAT TATACTCTCT CTCTGTGGGA AGGAGATTGT GGATATACTA

8301
GGGAAAATGC TACTCAAGCT AATCCTCTTT GTAAAAACTT TTATAATGAA

8351
TCTAAAAAAC ATTGGCACCC ATACGCATGT AGGTTTTGGA GATATAAAAA

8401
TGATAAAGAA GAGGTTAAGT GTAGAAATGA GGATAAAAAA CACTGTATTT

8451
ATTATCCCCT TTGGGATACC CCGGAAGCCT TATATGATTT TGGATTTTTG

8501
GCATATCTTA ATGCATTCCC TTCACCACTT TGTATTACAA ATCAAACTGT

8551
TAGGGAGCCA GAGTATGAAG TATATTCCTT ATATATGGAA TGTATGAATT

8601
CTGCGGAAAA ATATGGAATA GATAGTGTTT TGTTTGCTTT AAAAACTTTT

8651
TTAAATTTTA CTGGAACACC AGTGAATGAA ATGCCAACAG CCAGAGCATT

8701
TGTAGGCCTG ACTGATCCTA AATTCCCTCC AGTATATCCA AATATTACTA

-continued

8751
AAGAACGAAG AGGATGTGAC AATTCAAGAA GGAAAAGAAG AAGCACTAAT

8801
ATTGAAAAAC TTAGGTCAAT GGGATACTCA TTGACTGGAG CTGTGCAGAC

8851
CCTCTCACAA ATATCAGATA TAAATGATGA AAGACTTCAA CAAGGAGTTT

8901
ACTTATTGAG AGATCATGTT GTCACCTTAA TGGAAGCCGC CTTGCATGAT

8951
ATTACTATTA TGGAAGGAAT GTTAGCAATC GGTCATGTGC ATACCCACTT

9001
GAATCATCTT AAAACCATGT TACTAATGAG GAAGATTGAC TGGACTTTTA

9051
TTAAGAGTGA TTGGATTAAA GAACAACTTC AGAAAACTGA AGATGAAATG

9101
AAGATTATTA GAAGAACAGC TAAAAGTTTA GTATATTATG TGACTCAAAC

9151
ATCATCTTCC ACTACAGCAA CATCATGGGA AATTGGAATT TATTATGAAA

9201
TAACTATACC AAAACATATT TATTTGAATA ATTGGCAAGT TGTTAACATA

9251
GGTCATCTGA TTGAGTCAGC TGGTCATTTG ACCTTAATAA GGGTTAAACA

9301
TCCTTATGAA GACTTTAATA AAGAATGCAC ATATGAACAA TATTTACATC

9351
TTGAAGACTG CATATCTCAG GATTATGTGA TTTGTGACAC GGTACAAATA

9401
GTGTCACCAT GTGGAAACTC AACAGTAACC AGTGACTGCC CTGTCACTGC

9451
TGAAAAGGTA AAGGAACCAT ATATTCAAGT GTCAGCTTTA AAAAATGGAA

9501
GCTATTTGGT TCTAACCAGT AGAACAGATT GCTCAATACC AGCATATGTT

9551
CCCAGCATTG TAACTGTGAA CGAAACAGTT AAGTGTTTTG GGGTTGAGTT

9601
TCATAAACCA CTATACTCAG AAAGTAAAGT CAGCTTTGAA CCACAAGTTC

9651
CACATCTGAA ACTACGCTTG CCACATCTGG TTGGGATTAT TGCAAGTCTT

9701
CAAAATTTGG AAATTGAAGT AACCAGCACC CAAGAGAGTA TAAAAGATCA

-continued

9751
GATTGAAAGA GTTCAATCAC AGCTTCTTCG GCTGGACATT CACGAGGGAG

9801
ACTTTCCTGC TTGGATTCAA CAACTTGCTT CTGCAACCAA GGACGTCTGG

9851
CCTGCAGCTG CTAAAGCTCT TCAAGGCATA GGTAACTTTT TATCTAATAC

9901
TGCCCAGGGA ATATTTGGAA CTGCTGTAAG TATTCTATCC TATGCCAAGC

9951
CTATTCTTAT AGGAATAGGT GTTATACTTT TGATTGCATT CTTGTTTAAG

10001
ATTGTATCAT GGCTTCCTGG GAAGAAGAAA AAGAACTAGG ACATCTGCAT

10051
CTTCCAGAAG ACGATCCTCT GCCCAATTTA GATGTGCTCC TGGGTCTTGA

10101
TCATATGGAA TCCAATGAAG GACCTGATCA AAATCCAGGA GCTGAAAAGA

10151
TCTACATTCA ACTCCAAGCA GTCCCAGGGG AAGCCTCAGA GAAAACTTAC

10201
AAATTTGGAT ATGAAGACAA AGAGGCACAA AATCCTGACT TAAAAATGAG

10251
AAATTGGGTT CCTAACCCCG ACAAAATGAG TAAGTGGGCC TGTGCAAGGC

10301
TTATTCTTTG TGGACTTTAT AATGCAAAAA AGGCTGGAGA ACTCTTGGCT

10351
ATGGACTATA ATGTTCAATG GGAACAATCA AAAGAAGACC CAGGATACTT

10401
TGAAGTGGAA TATCACTGTA AAATGTGCAT GACTGTTATT CATGAACCTA

10451
TGCCTATCCA ATATGATGAA AAAACTGGAT TATGGCTAAA AATGGGTCCC

10501
CTTAGGGGAG ATATAGGATC TGTAGTACAT ACTTGTAGAA GGCATTACAT

10551
GAGATGTTTG TCTGCCCTTC CTAGCAATGG AGAACCTCTC AAACCTAGAG

10601
TCCGGGCTAA TCCTGTCCGA AGATATCGAG AGAAGCAAGA GTTCGTTGCG

10651
ACTAGGCCTA AACGCTCCAG ATGGGGTGTG GCCCCTAGCG CAGACTCCCA

10701
TACTTCCAGT GGTGACGCCA TGGCCCTTAT GCCAGGACCA TGCGGCCCCC

-continued

10751
TCGGTATGGA CACTCCTGGT TGCTTACTGG AAGGGATACA AGGATCAGGG

10801
CCTGGAACCT CCGAAATGGC TGTGGCAATG TCAGGAGGAC CTTTCTGGGA

10851
AGAAGTGTAT CGAGACTCAA TTCTTGGTGC CCCCACTGGG TCTAGTGAAA

10901
ATTAGGCTTT ATCAAAATCT AACTGTTGTA AATGTTTGTG GATCTGTTGA

10951
CCCATGGGAA AATGAGAATC CCACTAGAGG TCGCAGAGGG CCTATGCATA

11001
GATATGATTG TAGAATTGCT TGTGATCCAA GCTATTGCTT TAAGGCTATT

11051
TGGGAAGGAA ACTTTTGGGA CAAAAAAAAA AGGATCAGGC ATGCTGGCTA

11101
GTTCATCTGA AAGAAGGACA TAAATTTGGT GCAGATGAGT TATCTTCTGG

11151
GGATCTTAAA ATATTAGCAG AATCTAGACC TTATCCATAT GGATCTATTG

11201
GTCATTGTGC TATGCTTCAA TATGCAGTAC AAGTTAAAAT GAGAGTTGAT

11251
AGAGCTCCTT TGACCTCAAA GGTGAGAGCT ATTAAAGCTT TGCACTATCA

11301
TCGCTGGAAT ATTTGTCAGC TGGAAAATCC TGGCATAGGA GAGGGATTCA

11351
GTCCCTCTGG TAATACACAA GCTCTTAAAG CCTATGGACC TCAGCATGGA

11401
AGTGAAGAGG AGAGGGTGTG GCTGACAGCT ACTAAAATGA TTGGCACCCA

11451
GGAATCAGAC TATTGGCATG AGTACAAAAG ATGGGGATAT TTCCCTTTGA

11501
TTCCAAATAA ACATCATCCT GGGTGGACTA GACATCTTAC TAAATTCAAG

11551
ATATCTAGAT TCTCCACTCC TGCTGATGTC CAGAAAATTG TGGATGAGCT

11601
TCTCCCTAGA GGAGCAAGCA TTGTAATGCC AGATGGAACA AAGTATCCAA

11651
GTACCAGAAA AGTGCACTTA GTCAATGAAG GAACCCTTGT AGAATACCAA

11701
GCCAAATGTA AGGAGATAGA GGAAAAGTAC GGAGGATGCT TTTCTACAGA

-continued

11751
TAGTGATGAT GACAGTGATG ATTACTCTGA GGATACTCCA GAAACTGAAA

11801
CCACTGATGT GGAATAGAGT ACAGTGTTAA GGATTTACAT AATCTGCCTA

11851
GCAACTGCTT ATGCTTAAGA ATGAATCAGT ATATTGTTTA GGAATAAGCC

11901
TTAGTTTATA AGTAGTTAAT CCTTAGGGAG TATTTGGTGG AAATGACTGA

11951
GTGACATGAA GTTTATTCAC CATACTCTCA ATAGGAGCCA CTAGTTGAGC

12001
CTGTGCGTTC AAATCCATGC TCAGCTTAAG TGACTCCCTT TTAGTTTCAC

12051
TTTAAGTTAA GTTAGGAATA AGTTCCATAT AATCCTAAGG GAGTATGTGG

12101
ACCTTCTTGT TAGGAAATAG TTTAAGATAG TCCACAGCTC CCTTCTTTTT

12151
GAGTTCTAGT CTTTGTTAAG TTTGTTGGCT CATACAGATA AAGTGCTCAT

12201
TAAACAGGAA ACCGCAACCG GGTAAAGGTT AGCACAGTAA ATTAAGCTAG

12251
CAGTTACTCA AGAGCCCGGT AAGCATTCAA GTAGTTCGAA TCCCTTTAAT

12301
GCTGACGGAT TGCTCTTTAG TGAGGTGATG TAATCTGTTT TTGCAATCTG

12351
AAATGTGTGT TTGCACAGGA AGTTGTACAA GAAAGGGAAT GGCTAAACTT

12401
GTTACAGTTC GAACAAACAT TTAGCAATTT CCTTTGCTTT TGGAGTTCGA

12451
GCCTTGTACT TATACTTTGA GCATATGTAT TGTAACACCT AAGTATGGAA

12501
AAATCTCCAA GTATGAGTCA CGAGATGCTT GGCTCACTGC GTTGGACGAC

12551
TGGAAAGAAG CTTCAACAGT CGGGACAGCA TCTCGAAGAA GGCCTCCGGA

12601
ATGAAAGAGT GAAAAATGAA GTCTCCTCAT TCAGAGAGCC TTCTTTTAGA

12651
ATTTCAGGCA GAATAGAGTT TCCAATAGAA TAAACTTTTG TATTAGCAGA

12701
TAGATAGGAT ATATAATCTC TGCTTTAGAT TGTACGGGAG CTCACCACTA

-continued

```
12751
CTCGCTGCGT CGAGAGTGTT CGAGTCTCTC CAGGCTTGGT
AAGATATAAA

12801
CTTTGGTATT CTCTGTATTC TTATGATCCA ATATTACTCT
GCTTATAGAT

12851
TGTAATGGGC AATGGCAATG CTTTATCAAT GAATGATTTT
ATGGTGAATT

12901
AAGTTCATAT ATGTTTTAAG AAGTTTAACA ATAAACCGAC
TTAATTCGAG

12951
AACCAGATTT ATTAGTATTG TCTCTTTCTA TACTTTAAGT
AAAGTGAAAG

13001
GAGTTGTATA TTAGCCTTGC TTATAAGAGC CATCTAGTGG
TATAAGTGTG

13051 TACTACACTT ATCTAAA
```

Seq. IDs 1–5 can be used for all the molecular biological techniques known to those skilled in the art. Such uses include, but are not limited to, generation of probes and vectors containing the sequences, antisense sequences derived from such sequences, and proteins synthesized using the sequences. RNA and other nucleic acid derivatives are contemplated by the present invention.

Knowing the entire sequence of SFVHu-1, Seq, ID 5, allows for the deletion and insertion of exogenous genetic sequences for use of the virus in treatments such as gene therapy. Having the complete genomic sequence will allow for the creation of novel viral vectors for gene therapy, attenuated recombinant vaccines and live viral vectors for the treatment and prevention of diseases. These and other molecular biological and medical procedures and treatments are contemplated by the present invention.

The 5' sequenced region of SFVHu-1, shown in Seq ID 3, comprises the LTR (Long Terminal Repeat). In foamy viruses, the LTR aids in the replication of the virus. The LTR is transactivated by a virus-specific protein, and unlike related retrovirus, HIV (Human Immunodeficiency Virus), no human cellular transcription factors activate the virus. LTRs in retroviruses like HIV have conserved consensus sequences for cellular transcription factors.

According to sequence homology, SFVHu-1 Seq ID 3, the LTRs are stable. There has not been significant change in the sequence even after long passage in a human host. For gene therapy uses, this stability is very important. It also appears that the internal promoter, found in the 3' sequence, Seq ID 4, is also conserved. Thus, the transcriptionally important regions of SFVHu-1 are stable. This indicates that the virus is not acquiring human sequences that would cause it to possibly become virulent or at least cause disease in humans due to introduced mutations. SFVHu-1, because of this stability, is an excellent vector, vaccine or gene therapy agent for humans. This stability is surprising is light of the high instability of the LTR of the virus known as HFV, Human Foamy Virus. HFV was derived from a nasocarcinoma and is now believed not to be a human foamy virus, but a chimpanzee virus. The HFV LTR is unstable and has lots of deletions, thus making it an undesirable vector.

The foamy viruses are unique in that at the 3' end of the env gene there is an internal promoter, IP. ORF 1 codes for a transactivator protein, TAF. TAF activates IP. Once the virus infects the cell, a little TAF is made, this TAF activates the internal promoter IP, which then causes the virus to make lots of TAF. Once sufficient quantity of TAF is made, the TAF functions to initiate the promoter found in the 5' LTR.

ORF 2 has presently unknown function, though it is theorized that it is necessary for replication of the virus in vivo. Without all of ORF 2 present, the virus will replicate in vitro, but the existing paradigm, prior to the present invention, was that ORF 2 was required for in vivo replication. ORF 2 is a putative site for gene insertion. Surprisingly, it has been found in Seq. ID 4, that ORF 2 of SFVHu-1 has multiple stop codons that prevent its translation. SFVHu-1 has a 5 base insertion and a point mutation that prevent accurate translation of ORF 2. According to the existing theory for foamy virus replication in vitro discussed above, these mutation should prevent replication of SFVHu-1 in humans. Surprisingly, the inventors have found that SFVHu-1 has a high rate of replication in the human host. The virus is found in the peripheral blood lymphocytes (PBL) of the host and is cultured from such cells in tissue culture systems. Reverse transcriptase activity has been found in the PBLs and plasma of the infected host. Viral RNA of SFVHu-1 has been shown by viral RT-PCR in both PBLs and plasma of the infected host. No other foamy virus has shown this activity. The literature has reported that there has been no identification of foamy viral replication in humans, until now, with the present invention, no such replication has been shown.

Knowing the entire sequence for SFVHu-1, Seq. ID 5, allows for various uses of the virus and viral sequences. The env gene of SFVHu-1 is necessary for foamy virus entry into animal cells. The gene of the present invention is effective in permitting infection of cells in a human host. Thus, for example, the env gene is used for uptake of foreign DNA by a wide range of human cells. There has long been a need for vectors for getting foreign nucleic acids into cells, both in vivo and in vitro. The introduction of foreign or exogenous nucleic acids into cells has been a technological hurdle for many gene therapy applications and has now been solved by the virus and sequences of the present invention. The env sequences can be used with any vector known to those skilled in the art, and with any other genetic sequences of choice, to allow for entry of the nucleic acids into the cells.

In another embodiment of the present invention, sequences of the foamy virus of the present invention can be used for other molecular biological applications. Regions of the gag gene are important in packaging genetic material. For example, the gag sequence or regions of the sequence are incorporated into other vectors and direct the packaging of the resultant genetic material for the particular application desired, such as packaging recombinant sequences to make altered infectious virions. Regions of the pol gene are known to be critical for the stable integration of foreign/viral DNA into the host genome. Vectors comprising the pol gene sequences can be used to integrate any DNA into a genome. The foamy virus and sequences of the present invention infect human cells, and thus, these sequences are used with other foreign or exogenous sequences in humans in methods, including, but not limited to, entry into cells, packaging, and insertion into the genome. Additionally, methods of using the foamy virus and sequences of the present invention are not limited to human cells, but all cells that allow for infection or entry of the nucleic acids.

The present invention is directed to compositions and methods comprising a new spumavirus, SFVHu-1, particularly compositions and methods for the sequences of the viral genome. The virus was isolated from humans who had worked with nonhuman primates. The new spumavirus, or foamy virus, does not appear to cause any disease in the human hosts. The new virus of the present invention may be an excellent vector for gene therapy and for vaccination purposes. Additionally, the antibodies or other detection methods for detecting the new virus may be important in detecting the presence of this and related viruses for xenotransplantation. In addition, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to procaryotic, eucaryotic and viral vectors.

Many new and potentially useful technologies are being developed which use viral vectors and may form the basis of future medical cures and therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense molecules that seek out and destroy viral gene products. In tissue culture, antisense oligonucleotides have inhibited infections by herpesviruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the gene have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected. Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the viral vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The virus of the present invention may be used as a viral vector to provide the foreign nucleic acid sequences to the intracellular metabolic processes.

Additionally, gene therapy may be used as a method of delivering drugs in vivo. For example, if genes that code for therapeutic compounds can be delivered to endothelial cells, the gene products would have facilitated access to the blood stream. Additionally, cells could be infected with a retroviral vector such as the present invention carrying nucleic acid sequences coding for pharmaceutical agents that prevent infection from occurring in the retrovirally infected cells.

The novel spumavirus of the present invention can also be used a safe and effective vaccine agent. Genetic sequences for immunogenic proteins from a variety of infectious agents can be incorporated into the foamy virus RNA. Once inside a cell, the gene product is expressed and releases the immunizing peptide to the body's immune system. In another method, the virus of the present invention can be used to immunize the body against cell markers found on cancer or tumor cells. The genetic sequence of the cancer cell marker is incorporated into the foamy virus RNA and after infection with the virus, the expressed gene product stimulates the immune system. The patient's immune system is used to remove the cancerous cells, obviating the need for chemotherapeutic methods.

The antibodies of the present invention can be used to detect the presence of the virus or viral particles of the present invention. These antibodies can be used in diagnostic or screening kits to assess the present of the virus. Additionally, the antibodies can be used to screen organs from nonhuman primates that may be used in humans. Detection of the presence of a virus that is transmitted from nonhuman primates to humans would be crucial in providing virus-free organs for transplantation.

The virus of the present invention can be used for the treatment of conditions due to the presence of rapidly dividing cells. In a host, the ability of SFVHu-1 to productively infect dividing cells provides an excellent treatment for conditions due to the presence of rapidly dividing cells. For example, a person with disease due to rapidly dividing cells, including but limited to cancer or any known angiogenic condition, could be infected with SFVHu-1. Such virus may or may not carry other, exogenous genes for other effects in the host. Because SFVHu-1 does not cause disease in the host and there is no transmission of the virus to contacts with the host, only the person with the condition due to rapidly dividing cells will be treated. In addition, only the rapidly dividing cells of that host person will be productively infected by SFVHu-1. Other cells in the body may be infected but will not be killed because the infection in nondividing cells is not productive. The virus will productively infect the rapidly dividing cells and kill them. For example, a person with a fast growing tumor would be infected with SFVHu-1 and the cells of the tumor would be destroyed by the virus. Additionally, the virus may be given to a person prior to the person developing a condition caused by dividing cells, and when the cells begin dividing, the virus would then undergo a productive infection and kill the cells. This therapy may halt or inhibit such conditions as leukemia or angiogenesis dependent diseases such as macular degeneration.

Such treatment with SFVHu-1 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels. Another such condition is cancer or tumor growth. Cancer or tumors include both solid tumors and other types. Infection with the virus of the present invention, which causes no disease and does not effect the host systemically, is an improvement over currently known treatments that involved systemically administered agents. Such chemotherapeutic agents kill rapidly dividing cells but also cause trauma to the entire person. The dosages of such chemotherapeutic agents must be titered between kiling the cancer and killing the patient.

In contrast, treatments of cancer with the present invention are not as harmful to the patient. The virus can either be administered systemically or injected in situ into the tumor. The virus will only replicate in rapidly dividing cells and will not effect cells that are not dividing. The infected cells are killed and tumor growth is stopped. The virus may be administered in one treatment or in a series of treatments.

The SFVHu-1 of the present invention can be recombinantly modified to be selective for cellular receptors on the tumor to make the virus even more specifically targeted to just those cells. Additionally, the virus may have altered promoter regions that can be selectively activated to cause a productive infection. The combination of different levels of control of the virus, both natural and recombinantly produced, are contemplated in the present invention. A virus could be made specific for attachment to only certain types of cellular receptors, for those cells that are dividing, and will only undergo replication if another exogenous promoter factor is present. Viral infection by two or more individually defective viruses, that require factors or promoters supplied by other foamy viruses or any type of virus, could provide for many levels of control of infection or treatment of specific conditions.

The virus may be administered to the host, for cancer treatment, gene therapy or vaccination by any methods known to those skilled in the art. Such methods include but are not limited to injection, inhalation, ingestion, topical administration and implantation. The virus may be killed or live, depending on the treatment considered.

The inventors of the present invention believe that the viruses of the present invention, comprising the isolates from Cases A, B, and C, and particularly Case A, are the first definitive isolation of an SFV-3-like spumavirus from persons exposed to nonhuman primates. The virus does not appear to cause disease and does not appear not transmitted to close household contacts or sexual contacts. This belief is supported by the epidemiology data, the PCR and sequencing data and the serology data.

The isolate from Case A, SFVHu-1, was deposited with the ATCC under the Budapest Treaty on Feb. 5, 1998, and was assigned ATCC no. VR-2596.

The present invention is further described by the examples which follow. Such examples, however, are not to be construed as limiting in any way either the spirit or scope of the present invention. In the examples, all parts are parts by weight unless stated otherwise.

EXAMPLE 1

Case A

Case A has intermittently been employed as a caretaker for non-human primates for twenty years between 1961 and 1997. Case A recalled multiple minor injuries and mucocutaneous exposures to non-human primate blood, body fluids, or fresh tissue. In addition, Case A was twice bitten by African green monkeys in the 1960s or early 70s. These injuries 52 were severe enough to require 7–10 stitches each. Case A is single and in good health. No sera collected from Case A prior to 1995 or from sexual partners are currently available for testing. Retrospective analysis of sera archived from Case A in 1995 showed the sera to have antibodies to SFV. (See FIG. 3, lane 2).

Figure 3:
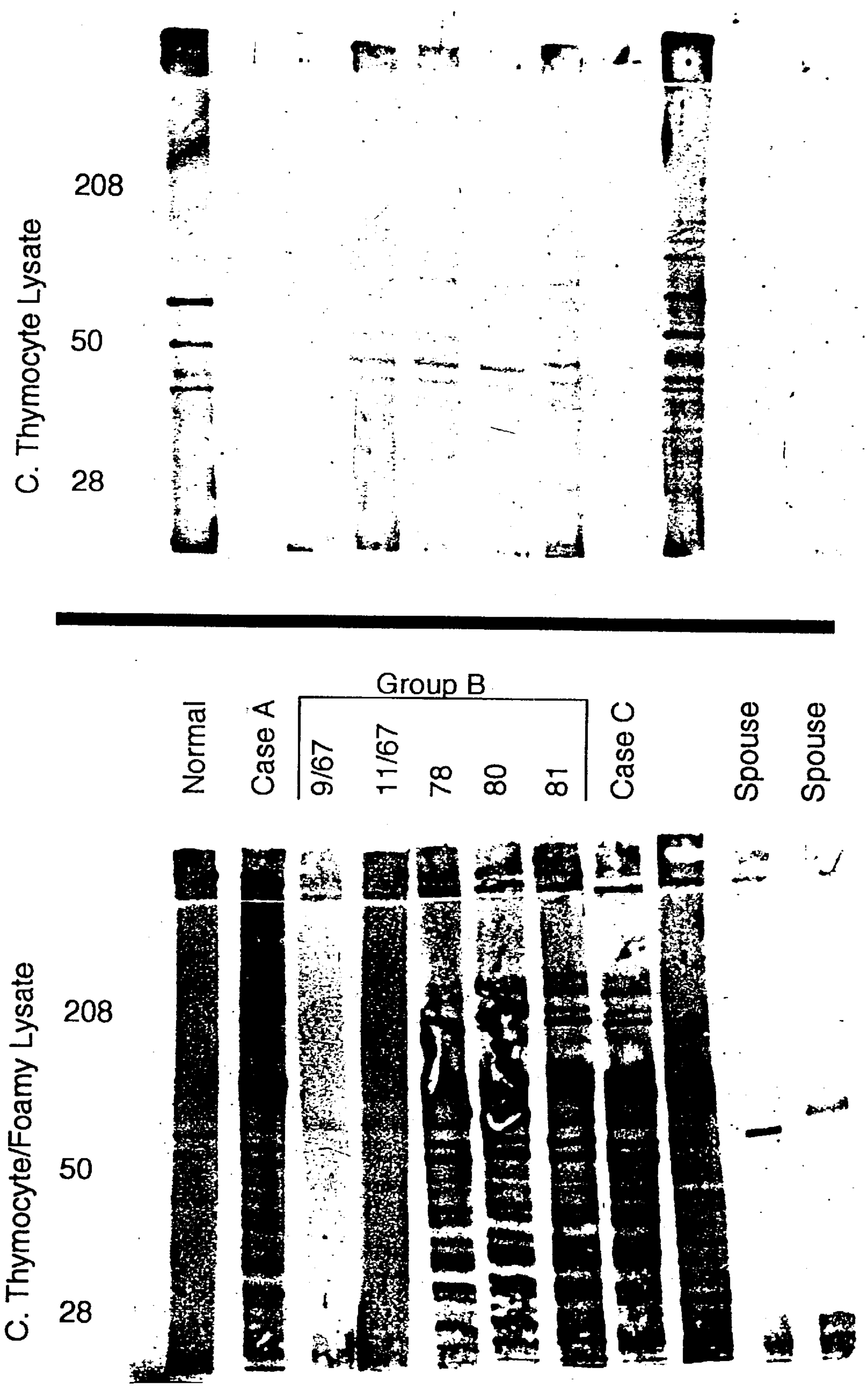
FIG. 3 is a Western blot of sera from Case A, Case B and Case C and the sera of spouses of two of the cases. The sera was tested against the whole cell lysate from Cf2Th cells infected with the spumavirus isolate. Whole cell lysate of uninfected Cf2Th were used as a control for seroreactivity towards nonviral proteins. In addition, the sera of Case B provides a view of the history of infection because of the existence of Case B sera obtained in 1967, and in 1978, 1980, and 1981.
Figure 4:
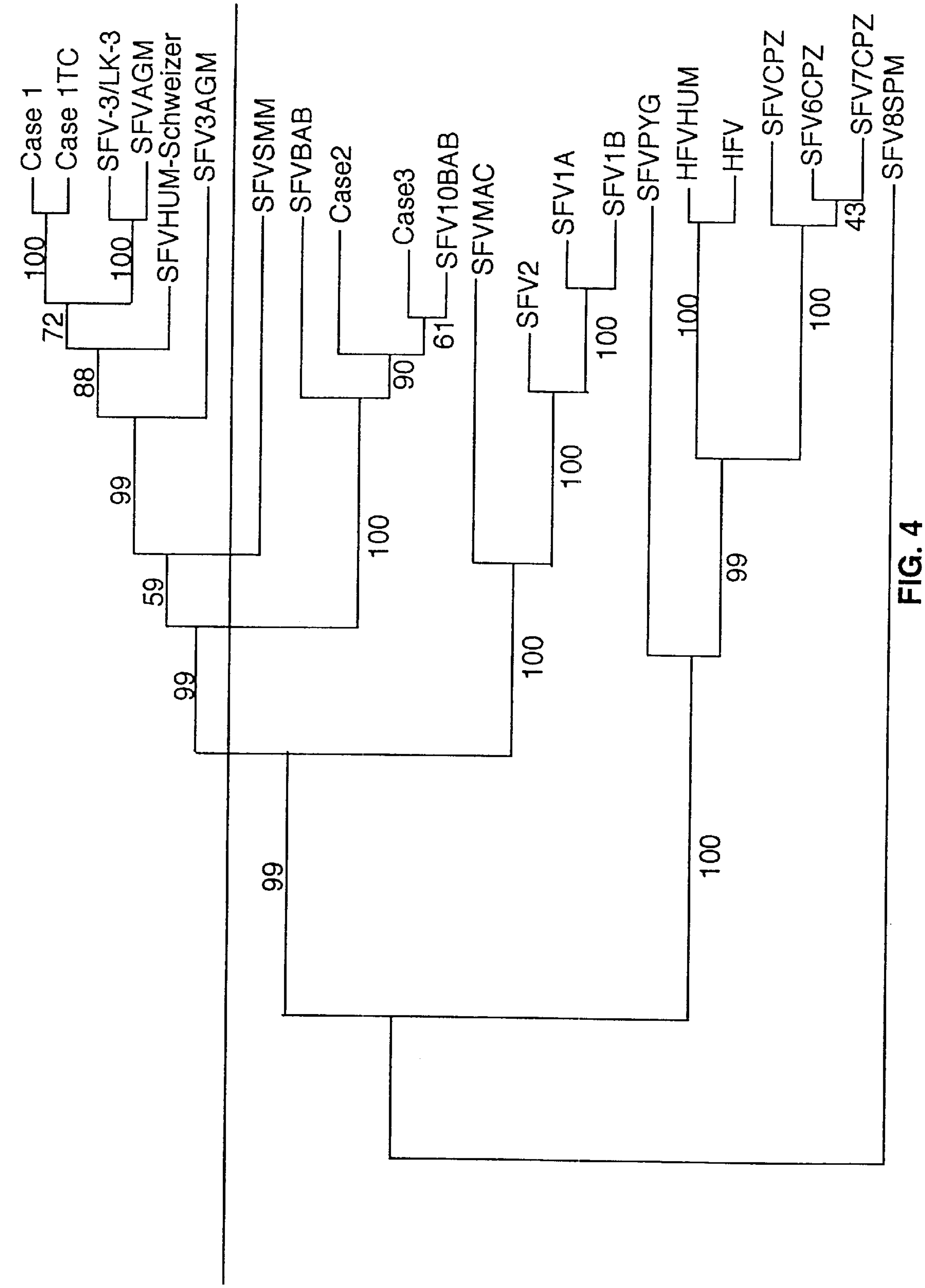
FIG. 4 is a phylogenetic tree showing the relationships between the sequences of the viruses of the novel spumavirus of the present invention and known spumaviruses.

The western blot of FIG. 3 shows whole cell lysate from Cf2Th cells infected with the spumavirus of the present invention tested in each individual lane with different antisera. In FIG. 3, particular viral proteins that show infection are the proteins with molecular weight of approximately 70–80 Daltons (p70 gag protein) and the proteins at approximately 130–140 Daltons (an envelope protein). The western blot of FIG. 3 shows whole cell lysate from Cf2Th cells infected with the spumavirus of the present invention. These proteins are not detectable in the western blot of FIG. 3 by normal sera, (lane 1) but are detectable by antisera from Case A.

EXAMPLE 2

Case B

Case B is a research scientist employed for three decades working with biologic specimens from non-human primates. Case B rarely reported injuries involving non-human primate blood, body fluids, or unfixed tissue, but did report an injury in 1970 when an unused needle was stuck through a glove that was potentially contaminated with baboon body fluids; and a 1972 cut inflicted by a broken capillary tube containing chimpanzee blood. Case B is in good health. Case B has been in a monogamous sexual relationship without use of barrier contraceptives or spermicides for over 20 years. Case B's spouse is negative for SFV-like infection by both serologic and PCR testing. Analysis of two serum specimens from Case B archived serially in 1967 were negative; sera archived in 1978 and subsequently were consistently seropositive. See FIG. 3, lanes 3 and 4 are the 1967 sera, lane 5 is sera from 1978, lane 6 is sera from 1980, lane 7 is sera from 1981. The sera of Case B's spouse is shown in lane 10.

EXAMLPE 3

Case C

Case C is an animal care supervisor who has worked with non-human primates for more than 3 decades. Case C recalls multiple minor injuries and mucocutaneous exposures to non-human primate blood, body fluids, or unfixed tissues. Case C reported a severe baboon bite around 1980 that required multiple stitches of an arm and hand. Case C is in good health except for type II diabetes mellitus. Case C has been in a monogamous sexual relationship for nearly three decades, during which barrier methods of contraception have not been employed and spermicides were used for no more than a 6 month period. Case C's spouse is negative for SFV-like infection by both serologic and PCR testing. Retrospective analysis of sera archived from Case C in 1988 showed the sera to have antibodies to SFV. See FIG. 3, lane 8 is Case C's sera from 1988, and lane 11 is sera from the spouse of Case C.

EXAMPLE 4

Western Blot Analysis

The sera from the three cases was analyzed by western blot analysis against whole cell lysates from Cf2Th cells infected by cell free supernatants from Cf2Th cells infected by a Case's PBLs. As shown in FIG. 3, Case A, Case B and Case C all show the characteristic gag proteins associated with the spumavirus. It is interesting to note that in Case B, Case B converted from negative to positive between 1967 and 1978. In addition, spouses of two of the Cases were negative.

EXAMPLE 5

Simian Foamy Virus Isolation

Peripheral blood lymphocytes (PBLs) were isolated from Cases A, B and C and were cultured with IL-2 for 48 hours, in RPI media with 10% fetal Calf serum, and penn-strep antibiotics. After 48 hours, the PBLs were added to the Cf2Th cells and co-cultured for 2–4 weeks. The cells were in DMEM supplemented with 2% nonessential amino acids, 20% fetal calf serum, and pen-strep antibiotics. 1 mL supernatants were collected from the cell cultures every 3 to 4 days and tested for amp-reverse transcriptase. Procedures for PBL treatment, culturing of Cf2Th cells and amp reverse transcriptase activity were procedures known to those in the art. For example, see Heneine, W., et al. "Detection of reverse transcriptase by a highly sensitive assay in sera from persons infected with HIV-1." (1995). J. Infectious Diseases, 171:1201–6.

EXAMPLE 6

Because of the positive amp-reverse transcriptase activity from cells from Case A, peripheral blood lymphocytes from Case A were cultured with IL-2 for 48 hours prior to addition to canine thymocytes (Cf2Th), human lung fibroblasts, and normal human peripheral blood lymphocytes. Supernatants were collected every 3 to 4 days and tested for amp-reverse transcriptase activity. Each time the 1 mL sample of supernatant was taken for amp-reverse transcriptase activity, a 5 mL sample of supernatant was taken and frozen at −80° C. in order to preserve a sample of the virus producing the amp-reverse transcriptase activity.

Figure 2:
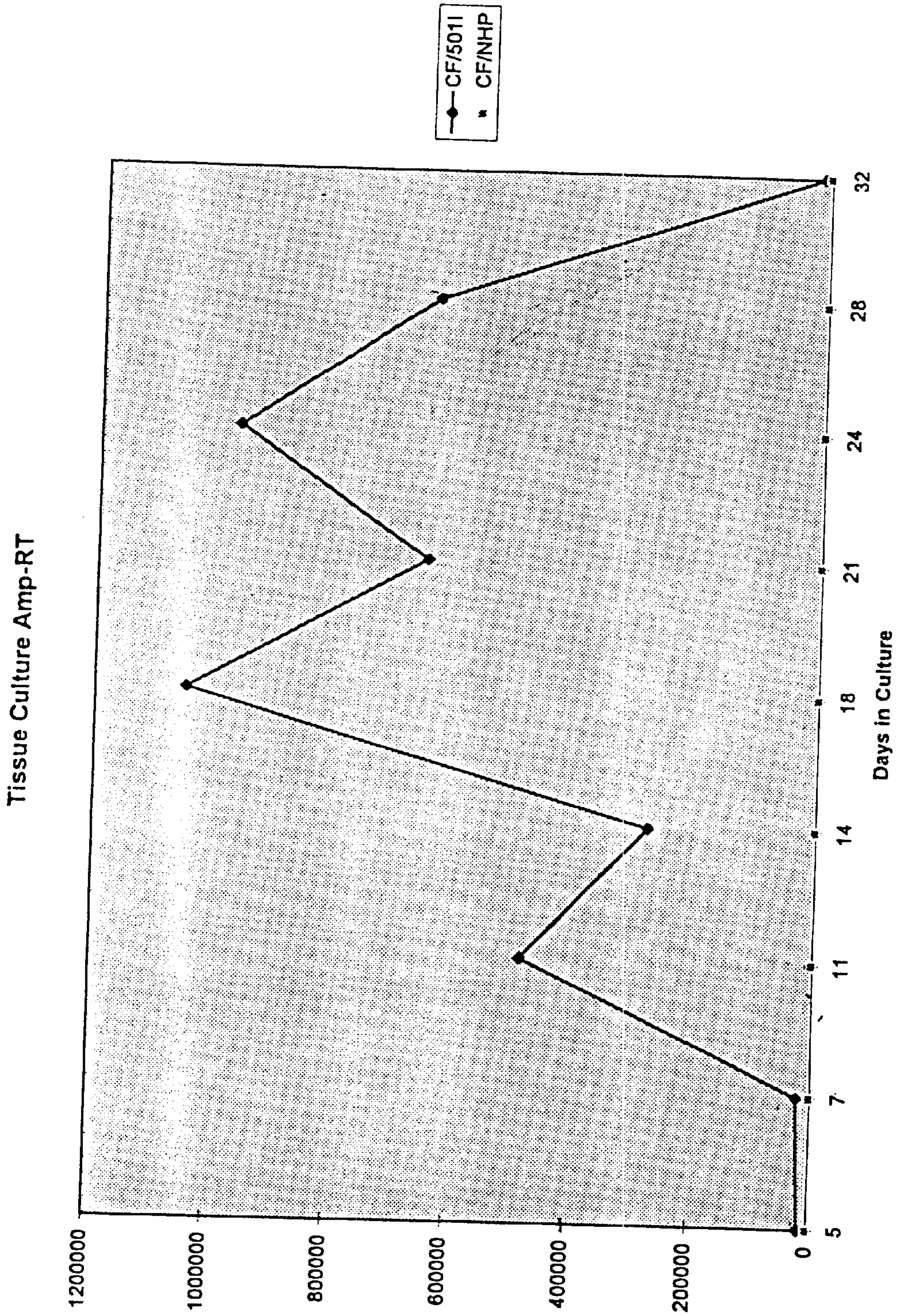
FIG. 2 shows tissue culture AMP-reverse transcriptase activity in canine thymocyte cells (Cf2Th) co-cultured with peripheral blood lymphocytes from an infected case worker. Along the baseline is another line showing control Cf2Th cells that were co-cultured with normal human peripheral blood lymphocytes, indicating there was no constitutive reverse transcriptase activity in these cultures .

At day 5, amp-reverse transcriptase testing showed a slightly positive signal in the canine thymocyte culture. The amp-reverse transcriptase activity increased over time. (See FIG. 2).

The activity in control Cf2Th cells that were treated as above, except for exposure to normal PBLs instead of infected PBLs, was shown by the lower line that overlaps the baseline.

There was no amp-reverse transcriptase activity inherently in these Cf2Th cells, providing evidence that there was no contamination by a retrovirus or spumavirus by the tissue culture cells.

EXAMPLE 7

At the peak of amp-reverse transcriptase activity as described in Example 5, cell-free supernatants were transferred to fresh Cf2Th growing at $2\times10^5$ cells/mL. At day 4 in the new culture, cytopathic effects and syncytia was observed. Transmission electron microscopy showed viral particles in and around the cells (See FIG. 1). Viral particles were isolated from these cultures and were stored at the Centers for Disease Control and were deposited at the ATCC.

The Cf2Th cells were obtained from the in-house cell culture facility of the Centers for Disease Control, but these cells can also be obtained from the American Type Culture Collection (Rockville, Md.). See Mergia et al., et al., "Cell tropism of the simian foamy virus type 1 (SFV-1)," J. Med. Primatol. 1996:25:2–7, for use of these cells.

Having thus described the invention, numerous changes and modifications thereof will be readily apparent to those having ordinary skill in the art, without departing from the spirit or scope of the invention.

---

What is claimed:

1. A method of detecting spumavirus infection, comprising, contacting a sample with antibodies that specifically bind SFVHu-1.

2. The method of claim 1, wherein the antibodies bind proteins of SFVHu-1.

3. The method of claim 1, wherein the antibodies bind antibodies that bind SFVHu-1.

4. The method of claim 2, wherein the proteins are coded for by a nucleic acid sequence of the nucleic acid of Seq. ID 4.

5. The method of claim 2, wherein the proteins are coded for by a nucleic acid sequence of the nucleic acid of Seq. ID. 5.

6. A method of detecting spumavirus infection, comprising:

a) contacting a sample with antibodies capable of binding SFVHu-1; and b) confirming the presence of SFVHu-1 in the sample.

7. The method of claim 6, wherein the antibodies bind proteins of SFVHu-1.

8. The method of claim 6, wherein the antibodies bind antibodies that bind SFVHu-1.

9. The method of claim 7, wherein the proteins are coded for by a nucleic acid sequence of the nucleic acid of Seq. ID 4.

10. The method of claim 7, wherein the proteins are coded for by a nucleic acid sequence of the nucleic acid of Seq. ID. 5.

* * * * *

SEQUENCE LISTING

```
<160> NUMBER OF SEQ ID NOS: 5

<210> SEQ ID NO 1
<211> LENGTH: 423
<212> TYPE: DNA
<213> ORGANISM: Human foamy virus

<400> SEQUENCE: 1

ttactacaag gacaatatcc aaaaggtttt ccaaaacaat atcaatatga acttaatgaa     60

ggacaagtta tagtaactcg tcctaatgga caaagaatta ttcctccaaa atcagacagg    120

cctcaaatta ttttgcaagc acataatatt gcacatacag gaagagattc aacctttctt    180

aaggtctctt ccaagtattg gtggccaaat cttagaaagg atgtggttaa agttatcaga    240

caatgtaagc aatgtctggt cacaaatgca gctaccttag ctgcgcctcc aatactgagg    300

cctgaaagac ctgtaaagcc ttttgataaa ttttttgttg actatattgg ccctttaccc    360

ccttctaatg ggtacttaca tgtccttgta gtagtcgatg gtatgactgg atttgtatgg    420

tta                                                                  423


<210> SEQ ID NO 2
<211> LENGTH: 423
<212> TYPE: DNA
```

-continued

<213> ORGANISM: Human foamy virus

<400> SEQUENCE: 2

```
ttactacaag gacaatatcc aaaaggtttt ccaaaacaat atcaatatga acttaatgaa     60
ggacaagtta tagtaactcg tcctaatgga caaagaatta ttcctccaaa atcagacagg    120
cctcaaatta ttttgcaagc acataatatt gcacatacag gaagagattc aacctttctt    180
aaggtctctt ccaagtattg gtggccaaat cttagaaagg atgtggttaa agttatcaga    240
caatgtaagc aatgtctggt cacaaatgca gctaccttag ctgcgcctcc aatactgagg    300
cctgaaagac ctgtaaagcc ttttgataaa ttttttgttg actatattgg ccctttaccc    360
ccttctaata ggtacttaca tgtccttgta gtagtcgatg gtatgactgg atttgtatgg    420
tta                                                                  423
```

<210> SEQ ID NO 3
<211> LENGTH: 1567
<212> TYPE: DNA
<213> ORGANISM: Human foamy virus

<400> SEQUENCE: 3

```
ttcccaataa acatcatcct gggtggacta gacatcttac taaattcaag atatctagat     60
tctccactcc tgctgatgtc cagaaaattg tggatgagct tctccctaga ggagcaagca    120
ttgtaatgcc tgatggaaca aagtatccaa gtaccagaaa agtgcactta gtcaatgaag    180
gaacccttgt agaataccaa gccaaatgta aggagataga ggaaaagtac ggaggatgct    240
tttctacaga tagtgatgat gacagtgatg attactctga ggatactcca gaaactgaaa    300
ccactgatgt ggaatagagt acagtgttaa ggattcacat aatctgccta gcaactgctt    360
atgcttaaga atgaatcagt atattgttta ggaataagtt atagtttata agaagttaat    420
ccttagggag tatttggtgg aaatgactga gtgacatgaa gtttattcac catactctca    480
ataggagcca ctagttgagc ctgtgcgttc aaatccatgc tcagcttaag tgactccctt    540
ttagtttcac tttaagttaa gttaggaata agttccatat aatcctaagg gagtatgtgg    600
accttcttgt taggaaatag tttaagatag tccacagctc ccttcttttt gagttctagt    660
ctttgttaag tttgttggct catacagata aagtgctcat taaacaggaa accgcaaccg    720
ggtaaaggtt agcacagtaa attaagctag cagttactca agagcccggt aagcattcaa    780
gtagttcgaa tccctttaat gctgacggat tgctctttag tgaggtgatg taatctgttt    840
ttgcaatctg aaatgtgtgt ttgcacagga agttgtacaa gaaagggaat ggctaaactt    900
gttacagttc gaacaaacat ttagcaattt cctttgcttt tggagttcga gccttgtact    960
tatactttga gcatatgtat tgtaacacct aagtatggaa aaatctccaa gtatgagtca   1020
cgagatgctt ggctcactgc gttggacgac tggaaagaag cttcaacagt cgggacagca   1080
tctcgaagaa ggcctccgga atgaaagagt gaaaaatgaa gtctcctcat tcagagagcc   1140
ttcttttaga atttcaggca gaatagagtt tccaatagaa taaacttttg tattagcaga   1200
tagataggat atataatctc tgctttagat tgtacgggag ctcaccacta ctcgctgcgt   1260
cgagagtgtt cgagtctctc caggcttggt aagatataaa ctttggtatt ctctgtattc   1320
ttatgatcca atattactct gcttatagat tgtaatgggc aatggcaatg ctttatcaat   1380
gaatgatttt atggtgaatt aagttcatat atgttttaag aagtttaaca ataaaccgac   1440
ttaattcgag aaccagattt attagtattg tctctttcta tactttaagt aaagtgaaag   1500
gagttgtata ttagccttgc ttataagagc catctagtgg tataagtgtg tactacactt   1560
```

-continued atctaaa 1567

<210> SEQ ID NO 4
<211> LENGTH: 2408
<212> TYPE: DNA
<213> ORGANISM: Human foamy virus
<220> FEATURE:
<221> NAME/KEY: misc_feature
<222> LOCATION: (763)..(763)
<223> OTHER INFORMATION: "n" = unknown
<221> NAME/KEY: misc_feature
<222> LOCATION: (782)..(782)
<223> OTHER INFORMATION: "n" = unknown

<400> SEQUENCE: 4
aaggggatgt tgagcaatcc aacatgtgca tacccacttg aatcatctta aaaccatgtt 60
actaatgagg aagattgact ggacttttat taagagtgat tggattaaag aacaacttca 120
gaaaactgaa gatgaaatga agattattag aagaacagct aaaagtttag tatattatgt 180
gactcaaaca tcatcttcca ctacagcaac atcatgggaa attggaattt attatgaaat 240
aactatacca aaacatattt atttgaataa ttggcaagtt gttaacatag gtcatctgat 300
tgagtcagct ggtcatttga ccttaataag ggttaaacat ccttatgaag actttaataa 360
agaatgcaca tatgaacaat atttacatct tgaagactgc atatctcagg attatgtgat 420
ttgtgacacg gtacaaatat tgtcaccatg tggaaactca acagtaacca gtgactgccc 480
tgtcactgct gaaaaggtaa aggaaccata tattcaagtg tcagctttaa aaaatggaag 540
ctatttggtt ctaaccagta gaacagattg ctcaatacca gcatatgttc ccagcattgt 600
aactgtgaac gaaacagtta agtgttttgg ggttgagttt cataaaccac tatactcaga 660
aagtaaagtc agctttgaac cacaagttcc acatctgaaa ctacgcttgc cacatctggt 720
tgggattatt gcaagtcttc aaaatttgga aattgaagta acnagcaccc aagagagtat 780
anaagatcag attgaaagag ttcaatcaca gcttcttcgg ctggacattc acgagggaga 840
ctttcctgct tggattcaac aacttgcttc tgcaaccaag gacgtctggc ctgcagctgc 900
taaagctctt caaggcatag gtaacttttt atctaatact gcccagggaa tatttggaac 960
tgctgtaagt attctatcct atgccaagcc tattcttata ggaataggtg ttatactttt 1020
gattgcattc ttgtttaaga ttgtatcatg gcttcctggg aagaagaaaa agaactagga 1080
catctgcatc ttccagaaga cgatcctctg cccaatttag atgtgctcct gggtcttgat 1140
catatggaat ccaatgaagg acctgatcaa aatccaggag ctgaaaagat ctacattcaa 1200
ctccaagcag tcccagggga agcctcagag aaaacttaca aatttggata tgaagacaaa 1260
gaggcacaaa atcctgactt aaaaatgaga aattgggttc ctaaccccga caaaatgagt 1320
aagtgggcct gtgcaaggct tattctttgt ggactttata atgcaaaaaa ggctggagaa 1380
ctcttggcta tggactataa tgttcaatgg gaacaatcaa aagaagaccc aggatacttt 1440
gaagtggaat atcactgtaa aatgtgcatg actgttattc atgaacctat gcctatccaa 1500
tatgatgaaa aaactggatt atggctaaaa atgggtcccc ttaggggaga tataggatct 1560
gtagtacata cttgtagaag gcattacatg agatgtttgt ctgcccttcc tagcaatgga 1620
gaacctctca aacctagagt ccgggctaat cctgtccgaa gatatcgaga gaagcaagag 1680
ttcgttgcga ctaggcctaa acgctccaga tggggtgtgg cccctagcgc agactcccat 1740
acttccagtg gtgacgccat ggcccttatg ccaggaccat gcggcccctt cggtatggac 1800
actcctggtt gcttactgga agggatacaa ggatcagggc ctggaacctc cgaaatggct 1860

-continued

```
gtggcaatgt caggaggacc tttctgggaa gaagtgtacc gggactcaat tcctggtgcc   1920
cccactgggt ctagtgaaaa ttaggcttta tcaaaatcta actgttgtaa atgtttgtgg   1980
atctgttgac ccatgggaaa atgagaatcc cactagaggt cgcagagggc ctatgcatag   2040
atatgattgt agaattgctt gtgatccaag ctattgcttt aaggctattt gggaaggaaa   2100
cttttgggac aaaaaaaaaa ggatcaggca tgctggctag ttcatctgaa agaaggacat   2160
aaatttggtg cagatgagtt atcttctggg gatcttaaaa tattagcaga atctagacct   2220
tatccatatg gatctattgg tcattgtgct atgcttcaat atgcagtaca agttaaaatg   2280
agagttgata gagctccttt gacctcaaag gtgagagcta ttaaagcttt gcactatcat   2340
cgctggaata tttgtcagct ggaaaatcct ggcataggag aaggattcag tccctctggt   2400
aatacaca                                                            2408
```

<210> SEQ ID NO 5
<211> LENGTH: 13067
<212> TYPE: DNA
<213> ORGANISM: Human foamy virus
<220> FEATURE:
<221> NAME/KEY: misc_feature
<222> LOCATION: (6670)..(6670)
<223> OTHER INFORMATION: “n” = unknown
<221> NAME/KEY: misc_feature
<222> LOCATION: (7803)..(7803)
<223> OTHER INFORMATION: “n” = unknown

<400> SEQUENCE: 5

```
tgtggctgac agctactaaa atgattggca cccaggaatc agactattgg catgagtaca     60
aaagatgggg atatttccct ttgattccaa ataaacatca tcctgggtgg actagacatc    120
ttactaaatt caagatatct agattctcca ctcctgctga tgtccagaaa attgtggatg    180
agcttctccc tagaggagca agcattgtaa tgccagatgg aacaaagtat ccaagtacca    240
gaaaagtgca cttagtcaat gaaggaaccc ttgtagaata ccaagccaaa tgtaaggaga    300
tagaggaaaa gtacggagga tgcttttcta cagatagtga tgatgacagt gatgattact    360
ctgaggatac tccagaaact gaaaccactg atgtggaata gagtacagtg ttaaggattt    420
acataatctg cctagcaact gcttatgctt aagaatgaat cagtatattg tttaggaata    480
agccttagtt tataagtagt taatccttag ggagtatttg gtggaaatga ctgagtgaca    540
tgaagtttat tcaccatact ctcaatagga gccactagtt gagcctgtgc gttcaaatcc    600
atgctcagct taagtgactc ccttttagtt tcactttaag ttaagttagg aataagttcc    660
atataatcct aagggagtat gtggaccttc ttgttaggaa atagtttaag atagtccaca    720
gctcccttct ttttgagttc tagtctttgt taagtttgtt ggctcataca gataaagtgc    780
tcattaaaca ggaaaccgca accgggtaaa ggttagcaca gtaaattaag ctagcagtta    840
ctcaagagcc cggtaagcat tcaagtagtt cgaatccctt taatgctgac ggattgctct    900
ttagtgaggt gatgtaatct gtttttgcaa tctgaaatgt gtgtttgcac aggaagttgt    960
acaagaaagg gaatggctaa acttgttaca gttcgaacaa acatttagca atttcctttg   1020
cttttggagt tcgagccttg tacttatact ttgagcatat gtattgtaac acctaagtat   1080
ggaaaaatct ccaagtatga gtcacgagat gcttggctca ctgcgttgga cgactggaaa   1140
gaagcttcaa cagtcgggac agcatctcga agaaggcctc cggaatgaaa gagtgaaaaa   1200
tgaagtctcc tcattcagag agccttcttt tagaatttca ggcagaatag agtttccaat   1260
agaataaact tttgtattag cagatagata ggatatataa tctctgcttt agattgtacg   1320
```

-continued

```
ggagctcacc actactcgct gcgtcgagag tgttcgagtc tctccaggct tggtaagata   1380
taaactttgg tattctctgt attcttatga tccaatatta ctctgcttat agattgtaat   1440
gggcaatggc aatgctttat caatgaatga ttttatggtg aattaagttc atatatgttt   1500
taagaagttt aacaataaac cgacttaatt cgagaaccag atttattagt attgtctctt   1560
tctatacttt aagtaaagtg aaaggagttg tatattagcc ttgcttataa gagccatcta   1620
gtggtataag tgtgtactta cacttatcta aagaggtgga attctttaag gataaccaat   1680
atacaaaatt ccacgacaat tggcgcccaa cgtggggctc gaatataagt cgggttttat   1740
tataaagact tgtttaagtc ttagaattat ccctagggac cttcacgcac tgcggaaggt   1800
ataagtactc aaagatgggt gatcataatt tgaatgttca agaactcttg aacctttttc   1860
agaatctagg tatttccaga caaccaaatc atagagaagt crtaggactt cgtatgacag   1920
gaggctggtg gggtccaggg acccgctata atctagtttc aatcttttta caagatgatt   1980
ctggacaacc tttacaacaa cccaggtgga gacctgaagg tagaccagtt aatcctttgg   2040
ttcataatac tatagaagcc ccttggggag acttaaggtt agcttttgaa gacttggatg   2100
tagcagaagg tactttgagg tttggtcctt tagctaatgg aaattggatt cctggagatg   2160
aatactccat ggaattccag cctccactag cacaagaaat agctcaatta caaagagacg   2220
aaatggaaga aatattggat ataacaggac aaatatgtgc acaagttata gatttagtag   2280
atatgcaaga tgctcaaatt agaggccytg aaagacgttt acaagataga ccaggtttaa   2340
gggataactt accagttgct ggtatacaag caccaccatc tagtccaatt gggcagccta   2400
ttgcatcatc ttcacttcaa cctgttcctg gatccagcca atcctctgct gatcttggtt   2460
gggaatcagg agcgcctggg caaatagatc ctagattgtc cagggtggcc tataacccat   2520
ttttaccagg accaagtgat gggtctgggg gatcaatccc agtccagcct agtgctcctc   2580
cagcggttct tccatcctta ccctcacttc ctgcacctgt tgctcaacct gttgttcagt   2640
atgttgttcc acctgcccct gctccacaag ctattccaat tcaacacatt cgagcagtga   2700
caggaaatac acctactaat ccaagagata ttcctatgtg gcttggaaga cattcagctg   2760
ctatagaagg agtatttcct atgactacgc ctgatcttcg ctgtcgagtt gttaatgctc   2820
ttataggagg aagtcttgga ctttctttgg agcctataca ttgtgtaaat tgggctgctg   2880
ttgtagctgc tctatatgtg agaacacatg gatcatatcc catacatgaa ctagctaatg   2940
tactccgagc agttgttaat caagagggag tagcaacagg ttttcaactt ggaattatgc   3000
tgtccaatca agattttaat cttgtttggg gaattctacg tcccctattg cctggacaag   3060
ctgtagtcac agctatgcag caaaracttg atcaagaagt cagtgacgct gctaggattg   3120
cctcctttaa tggacattta aatgatatat atcaacttct aggactgaat gcccgaggtc   3180
aaagcattac tagaactcag ggtagttcaa tctctggaac ctctacttct acaggcagag   3240
gaaggagagg acaaagaaac cagcaacagt ctggtcaaca gcaacaacaa caggcaagaa   3300
gaagtaatca gggaaaccag agacagagaa ataataatca gagacaatcc tctggtaata   3360
atcagggaca aggaggccaa ggaggatata atttgagacc cagaacttat cagccgcagc   3420
gctacggagg aggacgtgga agaagatgga acgataatca acaacagcaa caagcacagc   3480
caggcagatc agctgatcaa cctcgttccc agagtcagca accacaaaca gaggctcgtg   3540
gcgatcagtc acgaacatct ggtgctgggc gcggacaaca aggargaggg aaccaaaacc   3600
gaaatcaacg ccgggctgat gctaacaata ctcggaatgt ggatactgtg acagtaacca   3660
```

-continued

```
caacttcctc ctccacaact ggttcgggtc aaaatggatc ctctacagct cctccagccc   3720
ctggaagcag aaatcaaggg gactaaatta aaggctcatt gggacagtgg agctacagta   3780
acatgtgttc cacaagcctt tctagaagat gaagtaccaa ttaaaaatat ttggatcaag   3840
acaattcatg gtgaaaaaga acagcctgtc tattatttaa cctttaaaat mcaaggaaga   3900
aaagtagaag cagaagtaat ctcttcccct tatgactaca tattagtcag tccatctgac   3960
atcccctggc taatgaagaa acctctccaa ttgacaactt tagttcctct tcaagaatac   4020
aaagaaagac ttttaaagca aactatttta actgaaaaat ataaagatag attacaatct   4080
ttatttttga aatatgatgc attatggcaa cattgggaaa atcaagtggg ccataggcgt   4140
attaagcctc atcatatagc aactggtaca gttaacccta gaccacaaaa gcaatatcca   4200
attaatccaa aagcaaagcc aagtatacaa gttgtaatta atgatttatt aaaacaaggt   4260
gtgctaatac agcaaaatag tgtgatgaat actcctgtat atcctgtacc aaaaccagat   4320
ggaaaatgga gaatggtttt agattataga gaagtcaata agaccatccc tttaattgca   4380
gctcaaaatc aacattctgc agggattcta tcatccatat ttagaggcaa atataaaacc   4440
actttagatt tatctaatgg tttttgggct cattctatta caccagaatc ttattggtta   4500
actgctttta cttggcttgg acaacaatat tgttggacaa gattacctca aggatttctc   4560
aatagtcctg ctttatttac agcagatgtt gttgatttat taaaagaagt accaaatgta   4620
caagtttatg tggatgatat ttatattagt catgatgacc ctgaagaaca tttggaccaa   4680
cttgagaaag tgttttcgct attgctcaaa tgcggttatg ggtttctctt taaaaaatct   4740
gaaattgctc aacatgaagt tgaattcctt gggtttaata ttacaaaaga aggtcgaggc   4800
ctaacagaaa cttttaaaca aaaactctta aatataactc caccaaaaga tctgaaacag   4860
ttacaaagta ttttaggcct tctaaatttt gcaaggaact ttgttcctaa tttttctgaa   4920
ttagttaaac ccttatataa tatcattgct aatgccaatg agaaatatat tacatggact   4980
tctgacaata gtcaacagct acaatatata atttcattat taaattctgc agaaaactta   5040
gaagaaagaa atccagaagt cagattaata atgaaagtaa atacctctcc ttcagcagga   5100
tatatacggt tttataatga atttgctaaa agacctatta tgtacttgaa ttatgtttat   5160
actaaggcag aagttaagtt cactaacact gaaaaattgc taactactat acataaaggg   5220
ttaattagag ccttagatct tgccatggga caagaaatct tagtatatag tcctatcgta   5280
tccatgacca aaattcaaaa aacaccatta ccagaaagaa aagctctacc aattagatgg   5340
ataacctgga tgtcttattt agaagatccc agaatacaat ttcattatga taagacatta   5400
cccgagctac aacaggttcc tactgtcact gatgatgtta tagctaagac taaacatcct   5460
agtgaattta atatggtctt ctacactgat ggttctgcaa tcagacatcc aaatgttaat   5520
aagtcacata gtgctggaat gggtattgct caagtacagt ttaaacctga gtttacagtt   5580
gttaatactt ggtctattcc tcttggagat catacggcac aacttgccga agttgcagct   5640
gtagaatttg catgtaaaaa ggccctcaaa atagatggac ctgttttaat agtaactgat   5700
agtttctatg ttgctgagag tgctaataag gaattaccyt attggcaatc aaatgggttc   5760
tttaataaca aaaagaaacc ccttaaacat gtctccaagt ggaagtcaat tgcagaatgt   5820
gtacaattaa agcctgacat tactattatt catgaaaaag gtcaccagcc tactgcttca   5880
acatttcata cagaaggtaa taatttagct gataagcttg ccacccaagg aagttatgtg   5940
gtaaatacaa ataccactcc aagcctggat gcagagttgg atcaattact acaaggacaa   6000
tatccaaaag gttttccaaa acaatatcaa tatgaactta atgaaggaca agttatagta   6060
```

-continued

```
actcgtccta atggacaaag aattattcct ccaaaatcag acaggcctca aattattttg   6120
caagcacata atattgcaca tacaggaaga gattcaacct ttcttaaggt ctcttccaag   6180
tattggtggc caaatcttag aaaggatgtg gttaaagtta tcagacaatg taagcaatgt   6240
ctggtcacaa atgcagctac cttagctgcg cctccaatac tgaggcctga aagacctgta   6300
aagccttttg ataaattttt tgttgactat attggccctt tacccccttc taatrggtac   6360
ttacatgtcc ttgtagtagt cgatggtatg actggatttg tatggttata ccccactaag   6420
gctccttcaa ctggcgcaac tgttaaagct ctcaatatgc tcactagtat tgcagttcca   6480
aaggtgatac actctgatca gggtacagca ttcacctctg caacttttgc tgattgggca   6540
aaagacaaag gtatacattt ggaattcagt actccttacc atccccaaag tagtggcaag   6600
gtggaaagga aaaatagtga tataaaacga cttttaacta aactgcttgg tgggagacct   6660
gctaagtggn atgaccttct ttcagttgtt caattggcat taaataattc atataggcct   6720
ctttcttcta aatatactcc tcatcaactt ttgtttggta tagattcaaa tacaccattt   6780
gcaaactctg atacacttga tttatcaaga gaagaagaac tctctctttt acaggaaatc   6840
agaacttctc tttgccatcc atcctcccct cctgcctccg ttcgtgtctg gtctccttct   6900
gttggccaat tggtccagga gagggtagcc aggcctgcat ctttaagacc tcggtggcat   6960
aaacctactc ctgttctgga agtcattaat ccacgaactg ttgtcatttt ggaccatctt   7020
ggcaacagga gaactgtaag tgtggataat ttaaaattaa carcttatca gaaggatggc   7080
acctccaatg aatctgcagc aatggctatt gtggaaaaag atgaatgaag cacattcagc   7140
gttagagaat atttcaaccc ttactgaaga acagaagcaa caagtgatta ttgagattca   7200
acaagaagaa gtaataccta ctaggatgga cagagtaaag tatctagcat atgcatgttg   7260
tgctaccagt acacgtgtca tgtgttggtt atttttgatt tgtgtgttgc taattattgt   7320
atttgtatct tgttttgtca ctgttgctag gattcaatgg aataaggata ttactgtgtt   7380
tggaccagtc attgattgga atgttaccca tcaagcaaca tatcaacagc ttagagcttc   7440
cagaatagct agatctttaa gggtagaaca tcctcatata tcatatatat caataaatat   7500
gtctagtata ccacaaggtg ttatatatac acctcaccct gaacctataa tcctcaagga   7560
gagggtttta gggatttctc aggtgttaat gataaattct gaaaatatag ctaatgtggc   7620
caatttgtct caagacacaa aagtattgtt gactgatatg ataaatgagg aattacaaga   7680
tttgtcaaac caaatgattg acttcgaatt acctctagga gatcctagag accaaaatca   7740
atatgtacat cataagtgtt accaggagtt tgctcattgt tatttagtca aatataaaac   7800
acntaaagaa tggccctctt cagctctgat tgctgatcag tgtcccctac caggagaaca   7860
tccaactgta cagtattcac atcaaaatat atgggactat tatgttcctt ttcaacaaat   7920
acggccagag aaatggactt catccttagt atatgaagat gctagaatag ggagcttcta   7980
tataccaaaa aatatgagaa acaagaatgt tacacatgta atattttgtt cagatcaatt   8040
atatggaaaa tggtataatt tgatgaatac tgtacaagaa aatgaacaaa ttcaagtcat   8100
aaaattaaaa aatattacca aatcgggtac ctctcaagtt aaggatagag gacttccgtc   8160
cgcttggcat aagaatggta aaagtacata ttttaggcct attaatactt tggatatttg   8220
taatagacct gagttagtat tattactcaa tagtacttat tatactctct ctctgtggga   8280
aggagattgt ggatatacta gggaaaatgc tactcaagct aatcctcttt gtaaaaactt   8340
ttataatgaa tctaaaaaac attggcaccc atacgcatgt aggttttgga gatataaaaa   8400
```

-continued

```
tgataaagaa gaggttaagt gtagaaatga ggataaaaaa cactgtattt attatcccct   8460
ttgggatacc ccggaagcct tatatgattt tggatttttg gcatatctta atgcattccc   8520
ttcaccactt tgtattacaa atcaaactgt tagggagcca gagtatgaag tatattcctt   8580
atatatggaa tgtatgaatt ctgcggaaaa atatggaata gatagtgttt tgtttgcttt   8640
aaaaactttt ttaaatttta ctggaacacc agtgaatgaa atgccaacag ccagagcatt   8700
tgtaggcctg actgatccta aattccctcc agtatatcca aatattacta aagaacgaag   8760
aggatgtgac aattcaagaa ggaaaagaag aagcactaat attgaaaaac ttaggtcaat   8820
gggatactca ttgactggag ctgtgcagac cctctcacaa atatcagata taaatgatga   8880
aagacttcaa caaggagttt acttattgag agatcatgtt gtcaccttaa tggaagccgc   8940
cttgcatgat attactatta tggaaggaat gttagcaatc ggtcatgtgc atacccactt   9000
gaatcatctt aaaaccatgt tactaatgag gaagattgac tggactttta ttaagagtga   9060
ttggattaaa gaacaacttc agaaaactga agatgaaatg aagattatta gaagaacagc   9120
taaaagttta gtatattatg tgactcaaac atcatcttcc actacagcaa catcatggga   9180
aattggaatt tattatgaaa taactatacc aaaacatatt tatttgaata attggcaagt   9240
tgttaacata ggtcatctga ttgagtcagc tggtcatttg accttaataa gggttaaaca   9300
tccttatgaa gactttaata aagaatgcac atatgaacaa tatttacatc ttgaagactg   9360
catatctcag gattatgtga tttgtgacac ggtacaaata gtgtcaccat gtggaaactc   9420
aacagtaacc agtgactgcc ctgtcactgc tgaaaaggta aaggaaccat atattcaagt   9480
gtcagcttta aaaaatggaa gctatttggt tctaaccagt agaacagatt gctcaatacc   9540
agcatatgtt cccagcattg taactgtgaa cgaaacagtt aagtgttttg ggttgagttt   9600
tcataaacca ctatactcag aaagtaaagt cagctttgaa ccacaagttc cacatctgaa   9660
actacgcttg ccacatctgg ttgggattat tgcaagtctt caaaatttgg aaattgaagt   9720
aaccagcacc caagagagta taaaagatca gattgaaaga gttcaatcac agcttcttcg   9780
gctggacatt cacgagggag actttcctgc ttggattcaa caacttgctt ctgcaaccaa   9840
ggacgtctgg cctgcagctg ctaaagctct tcaaggcata ggtaactttt tatctaatac   9900
tgcccaggga atatttggaa ctgctgtaag tattctatcc tatgccaagc ctattcttat   9960
aggaataggt gttatacttt tgattgcatt cttgtttaag attgtatcat ggcttcctgg  10020
gaagaagaaa aagaactagg acatctgcat cttccagaag acgatcctct gcccaattta  10080
gatgtgctcc tgggtcttga tcatatggaa tccaatgaag gacctgatca aaatccagga  10140
gctgaaaaga tctacattca actccaagca gtcccagggg aagcctcaga gaaaacttac  10200
aaatttggat atgaagacaa agaggcacaa aatcctgact taaaaatgag aaattgggtt  10260
cctaaccccg acaaaatgag taagtgggcc tgtgcaaggc ttattctttg tggactttat  10320
aatgcaaaaa aggctggaga actcttggct atggactata atgttcaatg ggaacaatca  10380
aaagaagacc caggatactt tgaagtggaa tatcactgta aaatgtgcat gactgttatt  10440
catgaaccta tgcctatcca atatgatgaa aaaactggat tatggctaaa aatgggtccc  10500
cttaggggag atataggatc tgtagtacat acttgtagaa ggcattacat gagatgtttg  10560
tctgcccttc ctagcaatgg agaacctctc aaacctagag tccgggctaa tcctgtccga  10620
agatatcgag agaagcaaga gttcgttgcg actaggccta aacgctccag atggggtgtg  10680
gcccctagcg cagactccca tacttccagt ggtgacgcca tggcccttat gccaggacca  10740
tgcggccccc tcggtatgga cactcctggt tgcttactgg aagggataca aggatcaggg  10800
```

-continued

```
cctggaacct ccgaaatggc tgtggcaatg tcaggaggac ctttctggga agaagtgtat  10860
cgagactcaa ttcttggtgc ccccactggg tctagtgaaa attaggcttt atcaaaatct  10920
aactgttgta aatgtttgtg gatctgttga cccatgggaa aatgagaatc ccactagagg  10980
tcgcagaggg cctatgcata gatatgattg tagaattgct tgtgatccaa gctattgctt  11040
taaggctatt tgggaaggaa acttttggga caaaaaaaaa aggatcaggc atgctggcta  11100
gttcatctga aagaaggaca taaatttggt gcagatgagt tatcttctgg ggatcttaaa  11160
atattagcag aatctagacc ttatccatat ggatctattg gtcattgtgc tatgcttcaa  11220
tatgcagtac aagttaaaat gagagttgat agagctcctt tgacctcaaa ggtgagagct  11280
attaaagctt tgcactatca tcgctggaat atttgtcagc tggaaaatcc tggcatagga  11340
gagggattca gtccctctgg taatacacaa gctcttaaag cctatggacc tcagcatgga  11400
agtgaagagg agagggtgtg gctgacagct actaaaatga ttggcaccca ggaatcagac  11460
tattggcatg agtacaaaag atggggatat ttccctttga ttccaaataa acatcatcct  11520
gggtggacta gacatcttac taaattcaag atatctagat tctccactcc tgctgatgtc  11580
cagaaaattg tggatgagct tctccctaga ggagcaagca ttgtaatgcc agatggaaca  11640
aagtatccaa gtaccagaaa agtgcactta gtcaatgaag gaacccttgt agaataccaa  11700
gccaaatgta aggagataga ggaaaagtac ggaggatgct tttctacaga tagtgatgat  11760
gacagtgatg attactctga ggatactcca gaaactgaaa ccactgatgt ggaatagagt  11820
acagtgttaa ggatttacat aatctgccta gcaactgctt atgcttaaga atgaatcagt  11880
atattgttta ggaataagcc ttagtttata agtagttaat ccttagggag tatttggtgg  11940
aaatgactga gtgacatgaa gtttattcac catactctca ataggagcca ctagttgagc  12000
ctgtgcgttc aaatccatgc tcagcttaag tgactccctt ttagtttcac tttaagttaa  12060
gttaggaata agttccatat aatcctaagg gagtatgtgg accttcttgt taggaaatag  12120
tttaagatag tccacagctc ccttcttttt gagttctagt ctttgttaag tttgttggct  12180
catacagata aagtgctcat taaacaggaa accgcaaccg ggtaaaggtt agcacagtaa  12240
attaagctag cagttactca agagcccggt aagcattcaa gtagttcgaa tccctttaat  12300
gctgacggat tgctctttag tgaggtgatg taatctgttt ttgcaatctg aaatgtgtgt  12360
ttgcacagga agttgtacaa gaaagggaat ggctaaactt gttacagttc gaacaaacat  12420
ttagcaattt cctttgcttt tggagttcga gccttgtact tatactttga gcatatgtat  12480
tgtaacacct aagtatggaa aaatctccaa gtatgagtca cgagatgctt ggctcactgc  12540
gttggacgac tggaaagaag cttcaacagt cgggacagca tctcgaagaa ggcctccgga  12600
atgaaagagt gaaaaatgaa gtctcctcat tcagagagcc ttcttttaga atttcaggca  12660
gaatagagtt tccaatagaa taaacttttg tattagcaga tagataggat atataatctc  12720
tgctttagat tgtacgggag ctcaccacta ctcgctgcgt cgagagtgtt cgagtctctc  12780
caggcttggt aagatataaa ctttggtatt ctctgtattc ttatgatcca atattactct  12840
gcttatagat tgtaatgggc aatggcaatg ctttatcaat gaatgatttt atggtgaatt  12900
aagttcatat atgttttaag aagtttaaca ataaaccgac ttaattcgag aaccagattt  12960
attagtattg tctctttcta tactttaagt aaagtgaaag gagttgtata ttagccttgc  13020
ttataagagc catctagtgg tataagtgtg tactacactt atctaaa               13067
```